US009873663B2

(12) United States Patent
Oh et al.

(10) Patent No.: US 9,873,663 B2
(45) Date of Patent: Jan. 23, 2018

(54) FLUORENYL β-OXIME ESTER COMPOUNDS, PHOTOPOLYMERIZATION INITIATOR AND PHOTORESIST COMPOSITION CONTAINING THE SAME

(71) Applicants: SAMYANG CORPORATION, Seoul (KR); KOREA RESEARCH INSTITUTE OF CHEMICAL TECHNOLOGY, Daejeon (KR)

(72) Inventors: Chun-Rim Oh, Seoul (KR); Min-Sun Lee, Seoul (KR); Won-Jung Lee, Daejeon (KR); Yong-Il Cho, Gyeonggi-si (KR); Seung-Rim Shin, Daejeon (KR); Jong-Il Shin, Daejeon (KR); Sang-Oh Lee, Mokpo-si (KR); Kun Jun, Daejeon (KR)

(73) Assignees: Samyang Corporation, Seoul (KR); Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 15/112,087

(22) PCT Filed: Jan. 19, 2015

(86) PCT No.: PCT/KR2015/000535
§ 371 (c)(1),
(2) Date: Jul. 15, 2016

(87) PCT Pub. No.: WO2015/108386
PCT Pub. Date: Jul. 23, 2015

(65) Prior Publication Data
US 2016/0332960 A1 Nov. 17, 2016

(30) Foreign Application Priority Data

Jan. 17, 2014 (KR) ........................ 10-2014-0006344

(51) Int. Cl.
| | | |
|---|---|---|
| G03F 7/004 | (2006.01) |
| C07C 251/66 | (2006.01) |
| G03F 7/031 | (2006.01) |
| G02B 5/00 | (2006.01) |
| G02B 5/22 | (2006.01) |
| G03F 7/00 | (2006.01) |
| G03F 7/033 | (2006.01) |

(52) U.S. Cl.
CPC ............ *C07C 251/66* (2013.01); *G02B 5/003* (2013.01); *G02B 5/223* (2013.01); *G03F 7/0007* (2013.01); *G03F 7/0045* (2013.01); *G03F 7/031* (2013.01); *G03F 7/033* (2013.01); *C07C 2603/18* (2017.05)

(58) Field of Classification Search
CPC .......... G03F 7/004; G03F 7/027; G03F 7/031; G03F 7/007; G03F 7/032; C07C 251/66; C07C 251/68; C07C 2103/18
USPC ................... 430/281.1, 7, 311, 322; 548/444
See application file for complete search history.

(56) References Cited

U.S. PATENT DOCUMENTS

| | | | | |
|---|---|---|---|---|
| 7,648,738 B2* | 1/2010 | Tanabe | ............... | C07D 207/333 427/510 |
| 2001/0012596 A1* | 8/2001 | Kunimoto | .............. | A61K 6/083 430/138 |
| 2009/0042114 A1* | 2/2009 | Yamato | ................. | C07C 251/48 430/7 |
| 2010/0188765 A1* | 7/2010 | Matsumoto | .......... | C07D 409/06 359/891 |
| 2011/0129778 A1* | 6/2011 | Murata | ................. | C07C 251/66 430/281.1 |
| 2015/0056554 A1* | 2/2015 | Matsumoto | .......... | C07D 209/80 430/281.1 |
| 2015/0064624 A1* | 3/2015 | Nishimae | ............. | C07D 209/88 430/281.1 |
| 2015/0111152 A1 | 4/2015 | Shin et al. | | |

FOREIGN PATENT DOCUMENTS

| | | |
|---|---|---|
| EP | 2128132 A1 | 12/2009 |
| JP | 2001-233842 A | 8/2001 |
| JP | 2008-037930 A | 2/2008 |
| JP | 2010-156879 A | 7/2010 |
| WO | 2007/080947 A1 | 7/2007 |
| WO | 11-090217 A1 | 7/2011 |
| WO | 2012/045736 A1 | 4/2012 |
| WO | 2013/165207 A1 | 11/2013 |

* cited by examiner

*Primary Examiner* — Amanda C. Walke
(74) *Attorney, Agent, or Firm* — Nutter McClennen & Fish LLP; John J. Penny, Jr.

(57) ABSTRACT

The present invention relates to a novel β-oximester fluorene derivative compound, a photopolymerization initiator comprising the same, and a photoresist composition.

10 Claims, No Drawings

FLUORENYL β-OXIME ESTER COMPOUNDS, PHOTOPOLYMERIZATION INITIATOR AND PHOTORESIST COMPOSITION CONTAINING THE SAME

TECHNICAL FIELD

The present disclosure relates to novel fluorenyl β-oxime ester compounds and a photopolymerization initiator and a photoresist composition containing the same, and more particularly, a novel fluorenyl β-oxime ester compounds having remarkably superior sensitivity even in small amounts, a photopolymerization initiator containing the same, and a photoresist composition having outstanding properties such as a residual film thickness, pattern stability, chemical resistance and elasticity.

The present application claims priority under 35 U.S.C. § 119 to Korean Patent Application No. 10-2014-0006344 filed in the Republic of Korea on Jan. 17, 2014, and under 35 U.S.C. § 365 to PCT/KR2015/000535, filed on Jan. 19, 2015, the disclosures of which are incorporated herein by reference.

BACKGROUND

As a typical example of a photopolymerization initiator used in a photoresist composition, there have been know various types such as acetophenone derivatives, benzophenone derivatives, triazine derivatives, biimidazole derivatives, acylphosphine oxide derivatives and oxime ester derivatives, and among them, oxime ester derivatives have advantages; they absorb ultraviolet light almost without color and have high radical generation efficiency and good compatibility with photoresist composition materials and outstanding stability. However, oxime derivative compounds developed at an early stage have low photoinitiation efficiency, and especially, need to increase an exposure dose due to low sensitivity in a pattern exposure process, causing production amount reductions.

Thus, development of a photopolymerization initiator with high photosensitivity leads to achievement of sufficient sensitivity in small amounts, producing a cost saving effect, and exposure dose reductions due to high sensitivity, increasing a production amount.

A variety of oxime ester compound derivatives of formula 2 that can be used as a photopolymerization initiator in a photoresist composition are already known.

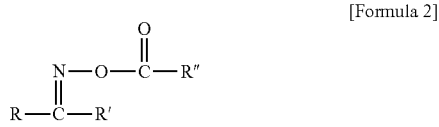

[Formula 2]

In the case of a photopolymerization initiator having an oxime ester group, it is easy to synthesize a variety of photopolymerization initiators capable of adjusting their absorption area by introducing appropriate substituents at R, R' and R" of a compound.

The oxime ester compound can polymerize and cure a polymerizable compound having an unsaturated bond when the photoresist composition is irradiated with light at 365-435 nm, and is being used for a black matrix, a color filter, a column spacer, an organic insulator film, and a photoresist composition for overcoating.

Accordingly, there has been a continuous demand for a novel photoinitiator that is suitable for a variety of uses because it satisfies the industrial requirements such as high sensitivity to a light source of long wavelengths of 365-435 nm and good photopolymerization reactivity, easy to manufacture, high thermal stability and storage stability, making it easy to handle, and a satisfactory solubility in a solvent (propylene glycol monomethyl ether acetate (PGMEA).

Recently, intensive research is being done on a photoresist composition used in a thin film display such as a liquid crystal display and an organic light emitting diode (OLED), to be more specific, a photoresist composition containing a high sensitivity photopolymerization initiator capable of forming a pattern for an organic insulator film of a liquid crystal display such as a thin film transistor liquid crystal display (TFT-LCD), a column spacer, an UV overcoat, R.G.B. color resist and a black matrix during development using an alkali developer solution.

Generally, a resist composition used to form a pattern preferably includes a photoresist composition containing a binder resin, a multifunctional monomer having an ethylenically unsaturated bond, and a photopolymerization initiator.

However, when forming a pattern using a conventional photopolymerization initiator, it needs to increase an amount of the photopolymerization initiator or an exposure dose due to low sensitivity in an exposure process for pattern formation, and its resulting disadvantage is that a mask is contaminated during the exposure process and by-products generated after decomposition of the photopolymerization initiator during crosslinking at high temperature reduce yields, and there is a production amount reduction problem due to the exposure process time increasing with the increasing exposure dose, and therefore, efforts are being made to solve the problems.

RELATED LITERATURES

Patent Literature

[Patent Literature 1] JP Patent Publication No. 2001-302871 (2001 Oct. 31)
[Patent Literature 2] PCT WO02/100903 (2002 Dec. 19)
[Patent Literature 3] JP Patent Publication No. 2006-160634 (2006 Jun. 22)
[Patent Literature 4] JP Patent Publication No. 2005-025169 (2005 Jan. 27)
[Patent Literature 5] JP Patent Publication No. 2005-242279 (2005 Sep. 8)
[Patent Literature 6] WO07/071497 (2007 Jun. 28)
[Patent Literature 7] WO08/138733 (2008 Nov. 20)
[Patent Literature 8] WO08/078686 (2008 Jul. 3)
[Patent Literature 9] WO09/081483 (2009 Jul. 2)
[Patent Literature 10] KR Patent Publication No. 2013-0049811 (2013 May 3)

DISCLOSURE

Technical Problem

The present disclosure is directed to providing novel fluorenyl β-oxime ester compounds, a photopolymerization initiator containing the same, and a photoresist composition having higher sensitivity with reduced amounts of them.

The present disclosure is further directed to providing a molded product formed by coating the photoresist composition.

Technical Solution

To achieve the above object, according to an aspect of the present disclosure, there is provided a fluorenyl β-oxime ester derivative compound of Formula 1:

[Formula 1]

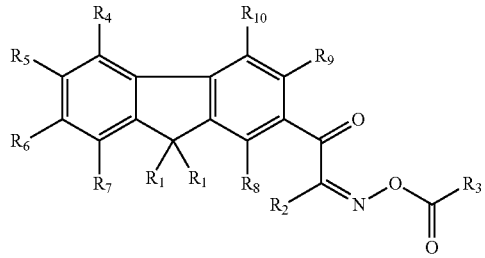

where $R_1$ to $R_{10}$ are each independently hydrogen, halogen, an alkyl group having 1-20 carbon atoms, an aryl group having 6-20 carbon atoms, an alkoxy group having 1-20 carbon atoms, an arylalkyl group having 7-40 carbon atoms, a hydroxyalkyl group having 1-20 carbon atoms, a hydroxyalkoxyalkyl group having 2-40 carbon atoms or a cycloalkyl group having 3-20 carbon atoms.

The $R_1$ to $R_{10}$ may be each independently hydrogen, bromo, chloro, iodo, a methyl group, an ethyl group, an n-propyl group, an i-propyl group, an n-butyl group, an i-butyl group, a t-butyl group, an n-pentyl group, an i-pentyl group, an n-hexyl group, an i-hexyl group, a phenyl group, a naphthyl group, a biphenyl group, a terphenyl group, an antryl group, an indenyl group, a phenantryl group, a methoxy group, an ethoxy group, an n-propyloxy group, an i-propyloxy group, an n-butoxy group, an i-butoxy group, a t-butoxy group, a hydroxymethyl group, a hydroxyethyl group, a hydroxyn-propyl group, a hydroxyn-butyl group, a hydroxyl-butyl group, a hydroxyn-pentyl group, a hydroxyi-pentyl group, a hydroxyn-hexyl group, a hydroxyi-hexyl group, a hydroxymethoxymethyl group, a hydroxymethoxyethyl group, a hydroxymethoxypropyl group, a hydroxymethoxybutyl group, a hydroxyethoxymethyl group, a hydroxyethoxyethyl group, a hydroxyethoxypropyl group, a hydroxyethoxybutyl group, a hydroxyethoxypentyl group or a hydroxyethoxyhexyl group.

The $R_1$ may be hydrogen, a methyl group, an ethyl group, a propyl group, or a butyl group; the $R_2$ may be a methyl group, an ethyl group, or a propyl group; the $R_3$ may be a methyl group, an ethyl group, a propyl group, or a butyl group; and the $R_4$ to $R_{10}$ may be hydrogen.

The fluorenyl β-oxime ester derivative compound may be selected from the following compounds:

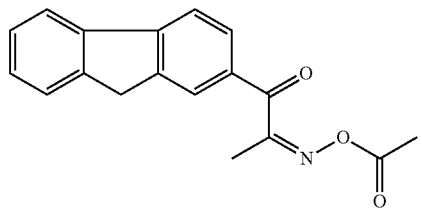

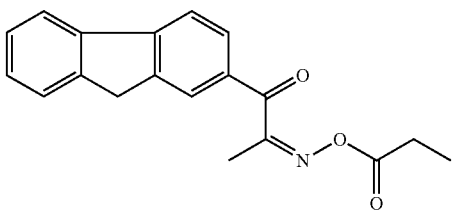

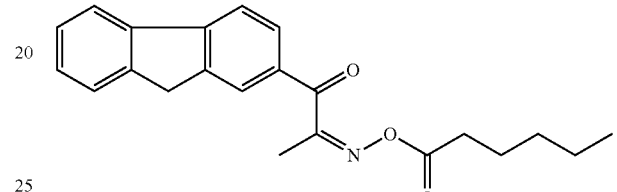

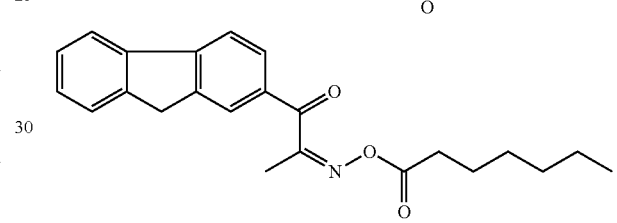

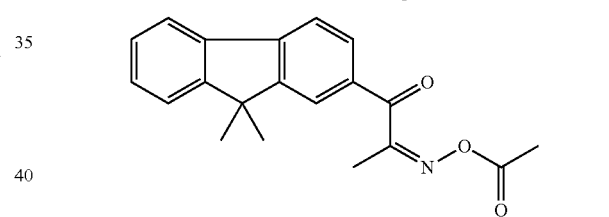

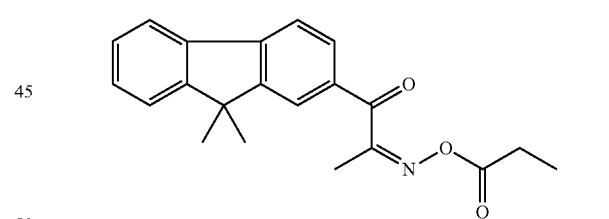

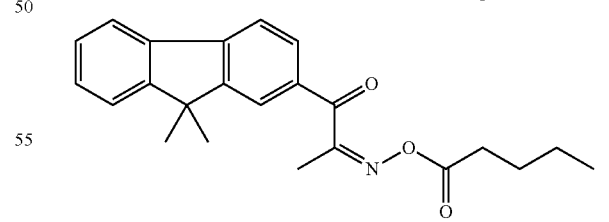

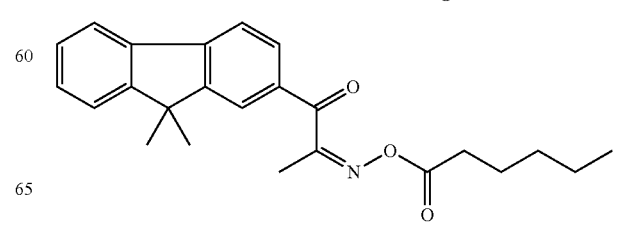

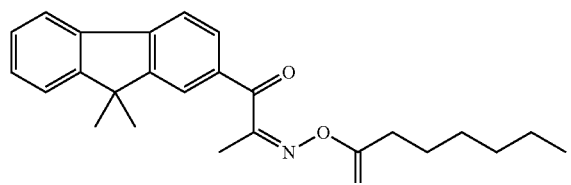
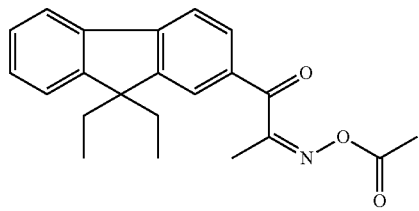
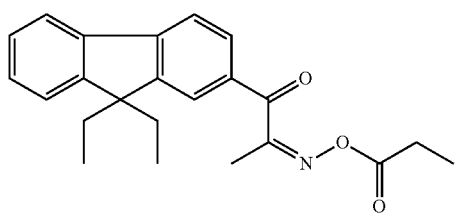
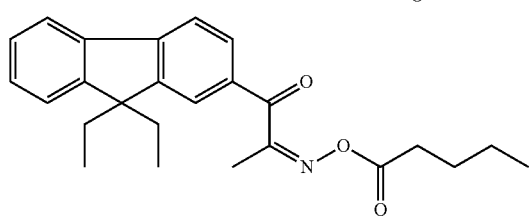
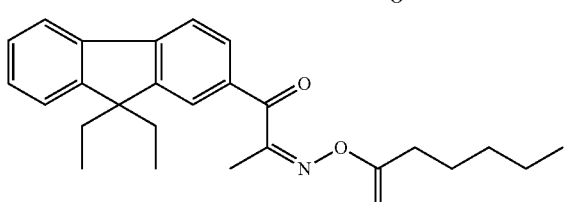
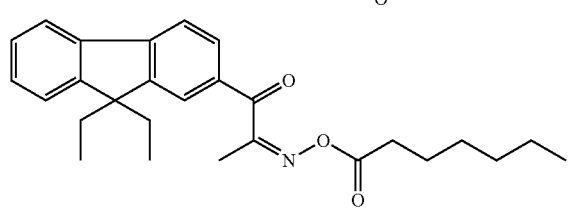
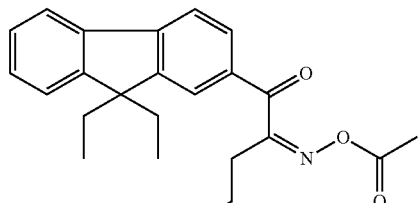
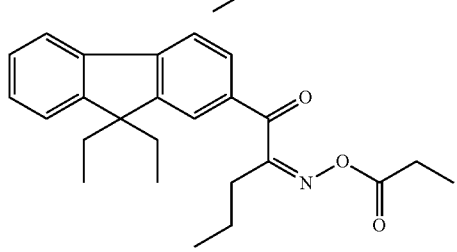
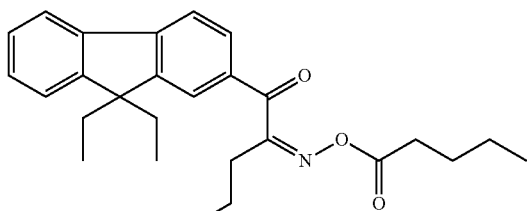
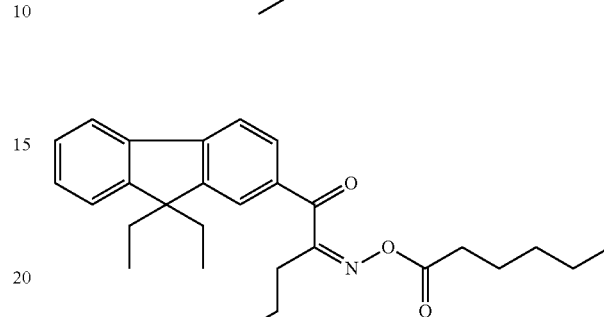
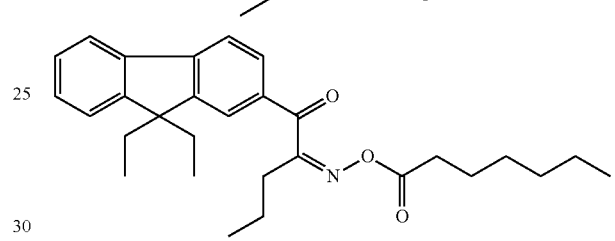
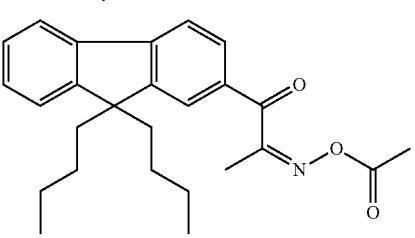
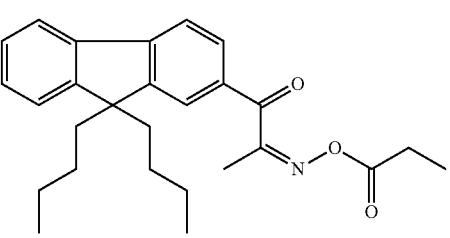
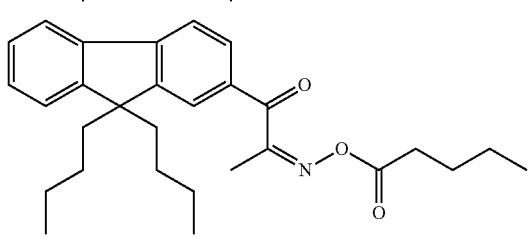
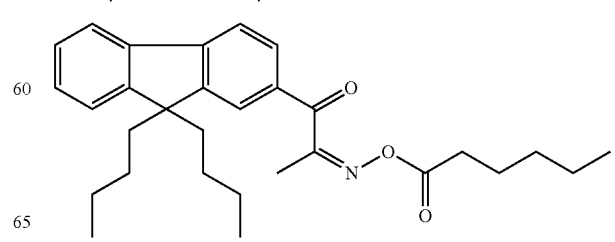

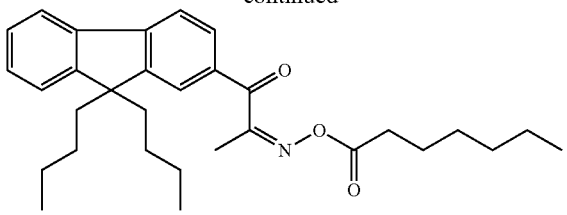

According to another aspect of the present disclosure, there is provided a photopolymerization initiator including the fluorenyl β-oxime ester derivative compound as an active ingredient.

According to another aspect of the present disclosure, there is provided a photoresist composition including the fluorenyl β-oxime ester derivative compound, an acrylic polymer or an acrylic polymer having an acrylic unsaturated bond on a side chain, a polymerizable compound having an ethylenically unsaturated bond, and a solvent.

The photoresist composition may include 0.01 to 10 wt % of a fluorenyl β-oxime ester derivative compound, 3 to 50 wt % of an acrylic polymer or an acrylic polymer having an acrylic unsaturated bond on a side chain, 0.001 to 40 wt % of a polymerizable compound having an ethylenically unsaturated bond, and 10 to 95 wt % of a solvent.

The photoresist composition may be used for a black matrix further comprising carbon black.

The photoresist composition may be used for a color filter further comprising a coloring material dispersion.

According to an aspect of the present disclosure, there is provided a molded product formed by coating the photoresist composition.

Effect of the Invention

Advantages of the fluorenyl β-oxime ester derivative compound of the present disclosure is that it has remarkably superior sensitivity even in small amounts when used as a photoinitiator of a photoresist composition, has outstanding properties such as a residual film thickness, pattern stability, chemical resistance and elasticity, and minimizes out-gassing generated from the photopolymerization initiator during exposure and post-baking processes in the manufacture of a thin film transistor liquid crystal display (TFT-LCD), thereby reducing contamination and minimizing defects that may occur therefrom.

MODE FOR CARRYING OUT THE INVENTION

Hereinafter, the present disclosure will be described in further detail. Prior to the description, it should be understood that the terms or words used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

Therefore, the configurations illustrated in the drawings and the embodiments are just preferable examples for the purpose of illustrations only, not intended to limit the scope of the disclosure, so it should be understood that a variety of other equivalents and modifications which can substitute them could be made at the time the application is filed.

The present disclosure provides a compound of Formula 1 and a photopolymerization initiator and a photoresist composition containing the same.

[Formula 1]

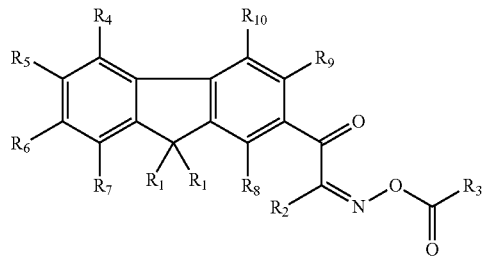

wherein $R_1$ to $R_{10}$ are each independently hydrogen, halogen, an alkyl group having 1-20 carbon atoms, an aryl group having 6-20 carbon atoms, an alkoxy group having 1-20 carbon atoms, an arylalkyl group having 7-40 carbon atoms, a hydroxyalkyl group having 1-20 carbon atoms, a hydroxyalkoxyalkyl group having 2-40 carbon atoms or a cycloalkyl group having 3-20 carbon atoms.

The term "alkyl group" as used herein refers to a straight chain type or side chain type of hydrocarbon chain radical that consists solely of carbon and hydrogen atoms, has no degree of unsaturation, and is attached to other fragments of a molecule by a single bond. The alkyl group is preferably a straight chain or branched alkyl group having 1 to 20 carbon atoms, more preferably a straight chain or branched alkyl group having 1 to 10 carbon atoms, and most preferably a straight chain or branched alkyl group having 1 to 6 carbon atoms. Examples of the unsubstituted alkyl group include a methyl group, an ethyl group, an n-propyl group, an isopropyl group, an n-butyl group, an isobutyl group, a sec-butyl group, a t-butyl group, a pentyl group, an isoamyl group, and a hexyl group. At least one hydrogen atom included in the alkyl group may be substituted by a halogen atom, a hydroxyl group, a thiol group (—SH), a nitro group, a cyano group, a saturated or unsaturated amino group, an amidino group, a hydrazine or hydrazone group, a carboxyl group, a sulfonic acid group, a phosphate group, a $C_1$-$C_{20}$ alkyl group, a $C_1$-$C_{20}$ halogenated alkyl group, a $C_1$-$C_{20}$ alkenyl group, a $C_1$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, or a $C_6$-$C_{20}$ heteroarylalkyl group.

The "alkoxy group" is preferably an oxygen-containing straight chain or branched alkoxy group each having a $C_1$-$C_{20}$ alkyl portion, more preferably an alkoxy group having 1 to 10 carbon atoms, and most preferably an alkoxy group having 1 to 4 carbon atoms. Examples of the alkoxy group include a methoxy group, an ethoxy group, a propoxy group, a butoxy group, and a t-butoxy group. The alkoxy group may be further substituted by at least one halo atom such as fluoro, chloro or bromo to provide a haloalkoxy group. Such examples include a fluoromethoxy group, a chloromethoxy group, a trifluoromethoxy group, a trifluoroethoxy group, a fluoroethoxy group and a fluoropropoxy group. At least one hydrogen atom in the alkoxy group may be substituted by a substituent in the same way as the alkyl group.

The "cycloalkyl group" includes hydrocarbon consisting of not only a single ring system but also two or more ring systems, and at least one hydrogen atom in the cycloalkyl group may be substituted by a substituent in the same way as the alkyl group. The cycloalkyl group is preferably a cycloalkyl group having 3 to 20 carbon atoms, more preferably a cycloalkyl group having 3 to 10 carbon atoms, and most preferably a cycloalkyl group having 3 to 8 carbon atoms.

The term "aryl group" as used herein refers to an aromatic monocyclic or multicyclic hydrocarbon ring system consisting only of hydrogen and carbon, and in this instance, the ring system may be saturated in whole or in part. At least one hydrogen atom in the aryl group may be substituted by a substituent in the same way as the alkyl group. The aryl group refers to a free radical induced from aromatic hydrocarbon by removal of one hydrogen, and includes a single or fused ring system containing, properly, 4 to 7 ring atoms, and preferably, 5 or 6 ring atoms in each ring, and includes even those containing multiple aryl linked by a single bond. The aryl group preferably has 6 to 20 carbon atoms, and more preferably 6 to 18 carbon atoms.

The term "hydroxyalkyl group" as used herein refers to an OH-alkyl group in which a hydroxyl group is bonded to the alkyl group defined above, and the term "hydroxyalkoxyalkyl group" as used herein refers to hydroxyalkyl-O-alkyl in which the hydroxyalkyl group and the alkyl group are bonded with oxygen. The hydroxyalkyl group preferably has 1 to 20 carbon atoms, more preferably 1 to 10 carbon atoms, and most preferably 1 to 6 carbon atoms. The hydroxyalkoxyalkyl group preferably has 2 to 40 carbon atoms, more preferably 2 to 20 carbon atoms, and most preferably 2 to 9 carbon atoms.

The "arylalkyl group" represents that at least one hydrogen atom in the alkyl group is substituted by the aryl group. The arylalkyl group preferably has 7 to 40 carbon atoms, more preferably 7 to 28 carbon atoms, and most preferably 7 to 24 carbon atoms.

More specifically, the $R_1$ to $R_{10}$ are each independently hydrogen, bromo, chloro, iodo, a methyl group, an ethyl group, an n-propyl group, an i-propyl group, an n-butyl group, an i-butyl group, a t-butyl group, an n-pentyl group, an i-pentyl group, an n-hexyl group, an i-hexyl group, a phenyl group, a naphthyl group, a biphenyl group, a terphenyl group, an antryl group, an indenyl group, a phenantryl group, a methoxy group, an ethoxy group, an n-propyloxy group, an i-propyloxy group, an n-butoxy group, an i-butoxy group, a t-butoxy group, a hydroxymethyl group, a hydroxyethyl group, a hydroxyn-propyl group, a hydroxyn-butyl group, a hydroxyi-butyl group, a hydroxyn-pentyl group, a hydroxyi-pentyl group, a hydroxyn-hexyl group, a hydroxyi-hexyl group, a hydroxymethoxymethyl group, a hydroxymethoxyethyl group, a hydroxymethoxypropyl group, a hydroxymethoxybutyl group, a hydroxyethoxymethyl group, a hydroxyethoxyethyl group, a hydroxyethoxypropyl group, a hydroxyethoxybutyl group, a hydroxyethoxypentyl group or a hydroxyethoxyhexyl group.

The $R_1$ may be hydrogen, a methyl group, an ethyl group, a propyl group, or a butyl group; the $R_2$ may be a methyl group, an ethyl group, or a propyl group; the $R_3$ may be a methyl group, an ethyl group, a propyl group, or a butyl group; and the $R_4$ to $R_{10}$ may be hydrogen.

The fluorenyl oxime ester derivative compound according to the present disclosure typically includes the following compound, but the following compound does not limit the present disclosure.

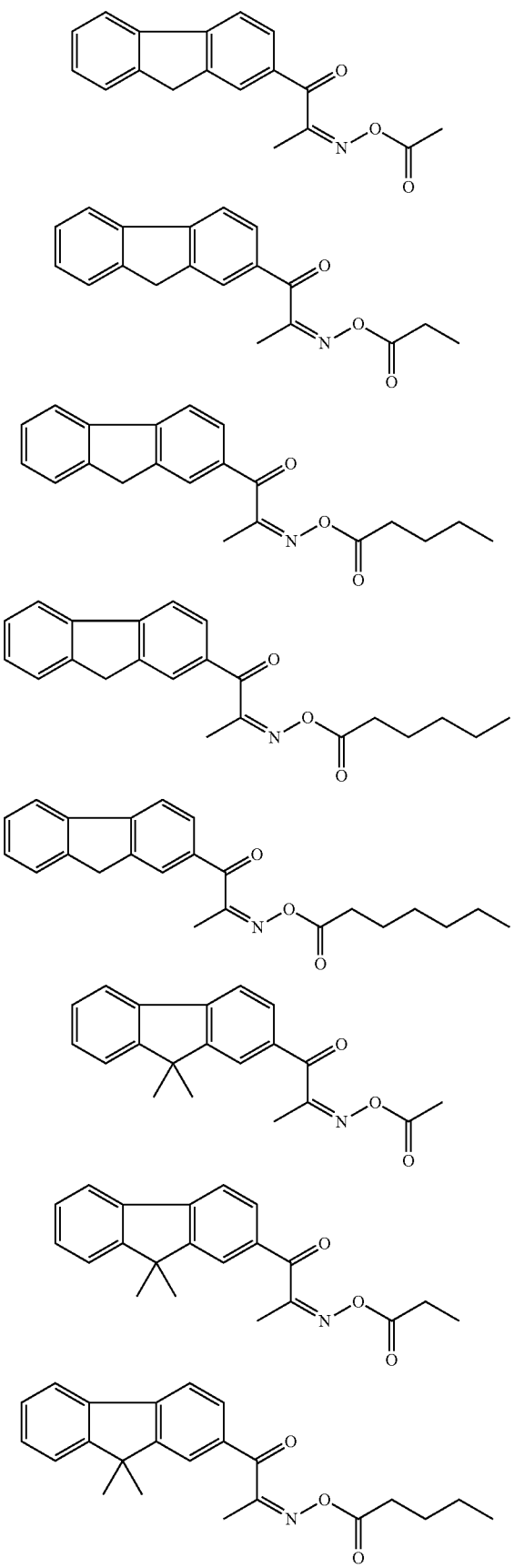

-continued

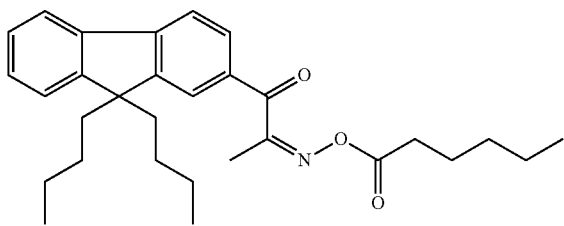

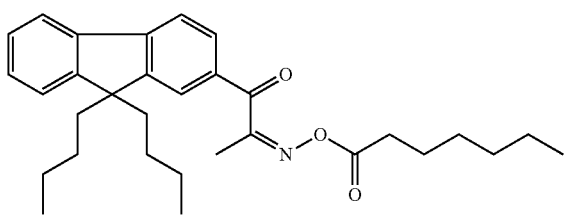

The fluorenyl oxime ester derivative compound of the above formula 1 according to the present disclosure may be prepared as shown in Reaction formula 1.

[Reaction formula 1]

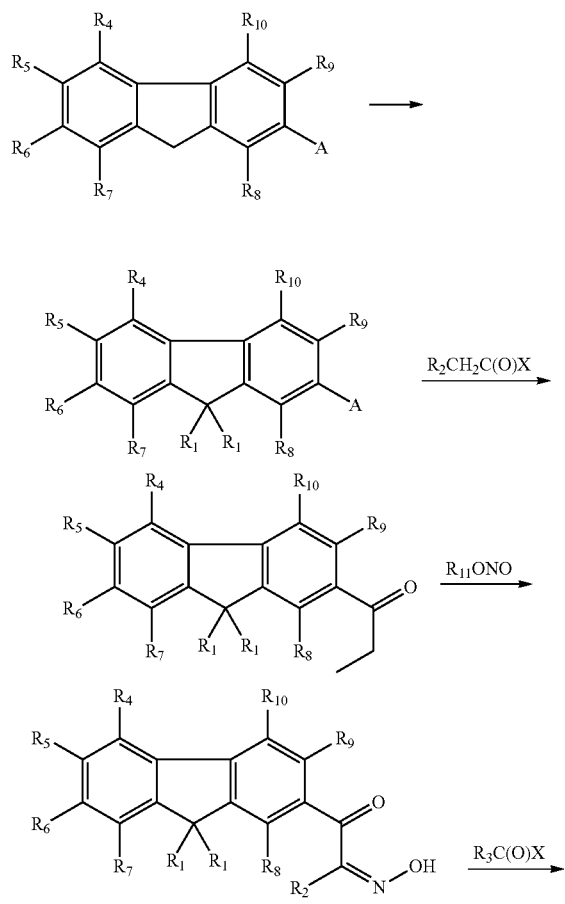

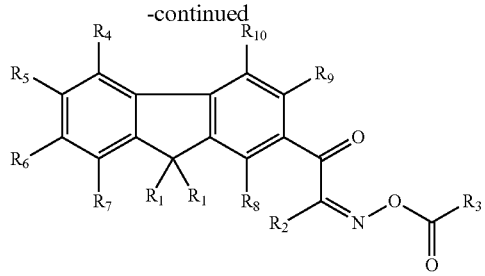

Wherein reaction formula 1, $R_1$ to $R_{11}$ and A are each independently hydrogen, halogen, an alkyl group having 1-20 carbon atoms, an aryl group having 6-20 carbon atoms, an alkoxy group having 1-20 carbon atoms, an arylalkyl group having 7-40 carbon atoms, a hydroxyalkyl group having 1-20 carbon atoms, a hydroxyalkoxyalkyl group having 2-40 carbon atoms or a cycloalkyl group having 3-20 carbon atoms, and X is halogen.

Further, according to an aspect of the present disclosure, there is provided a photopolymerization initiator including the fluorenyl β-oxime ester derivative compound of the above formula 1 as an active ingredient.

Further, according to an aspect of the present disclosure, there is provided a photoresist composition including the fluorenyl β-oxime ester derivative compound of the above formula 1.

In the present disclosure, the fluorenyl β-oxime ester derivative compound of the above formula 1 may be present as a photopolymerization initiator in the photoresist composition.

The photoresist composition of the present disclosure includes the fluorenyl β-oxime ester derivative compound of the above formula 1, an acrylic polymer or an acrylic polymer having an acrylic unsaturated bond on the side chain, a polymerizable compound having an ethylenically unsaturated bond, and a solvent, and is excellent in pattern characteristics adjustment and has outstanding thin film properties such as heat resistance and chemical resistance.

In the photoresist composition of the present disclosure, to adjust the pattern characteristics and impart the thin film properties such as heat resistance and chemical resistance, the acrylic polymer or the acrylic polymer having an acrylic unsaturated bond on the side chain used as the binder resin may be present in 3 to 50 wt %, preferably 10 to 40 wt %, and more preferably 15 to 30 wt %, based on 100 wt % of the photoresist composition.

The acrylic polymer preferably has a weight average molecular weight of from 2,000 to 300,000 and the degree of dispersion of from 1.0 to 10.0, and more preferably a weight average molecular weight of from 4,000 to 100,000.

The acrylic polymer is a polymer or copolymer of acrylic monomers such as acrylate, acrylic acid, and acrylic anhydride. Examples of the acrylic monomer include, but are not limited to, methylmethacrylate, ethylmethacrylate, propylmethacrylate, butylmethacrylate, pentylmethacrylate, hexylmethacrylate, cyclohexylmethacrylate, heptylmethacrylate, octylmethacrylate, nonylmethacrylate, decylmethacrylate, laurylmethacrylate, dodecylmethacrylate, tetradecylmethacrylate, hexadecylmethacrylate, isobornylmethacrylate, adamantylmethacrylate, dicyclopentanylmethacrylate, dicyclopentenylmethacrylate, benzylmethacrylate, 2-methoxyethylmethacrylate, 2-ethoxyethylmethacrylate, acrylic acid, methacrylic acid, itaconic acid, maleic acid, maleic anhydride, maleic acid monoalkyl ester, monoalkyl itaconate, monoalkyl fumarate, glycidylacrylate, glycidyl methacrylate, 3,4-epoxybutylmethacrylate, 2,3-epoxycyclohexyl methacrylate, 3,4-epoxycyclohexylmethylmethacrylate, 3-methyl oxetane-3-methylmethacrylate, and 3-ethyloxetane-3-methylmethacrylate.

Further, the acrylic polymer may be a copolymer obtained by polymerization of the above-mentioned acrylic monomers with one or more monomers of styrene, α-methylstyrene, acetoxystyrene, N-methylmaleimide, N-ethylmaleimide, N-propylmaleimide, N-butylmaleimide, N-cyclohexylmaleimide, methacrylamide, and N-methyl methacrylamide.

The acrylic polymer having an acrylic unsaturated bond on the side chain is a copolymer formed by an addition reaction of epoxy resin to an acrylic copolymer containing carboxylic acid, and includes binder resin obtained at the temperature of from 40 to 180° C. by an addition reaction of epoxy resin such as glycidylacrylate, glycidylmethacrylate, 3,4-epoxybutylmethacrylate, 2,3-epoxycyclohexylmethacrylate, and 3,4-epoxycyclohexylmethylmethacrylate to an acrylic copolymer containing carboxylic acid obtained by copolymerization of an acrylic monomer containing carboxylic acid, such as acrylic acid, methacrylic acid, itaconic acid, maleic acid and maleic acid monoalkyl ester, and at least two types of monomers of alkylmethacrylate such as methylmethacrylate and hexylmethacrylate, cyclohexylmethacrylate, isobornylmethacrylate, adamantylmethacrylate, dicyclopentanyl methacrylate, dicyclopentenylmethacrylate, benzylmethacrylate, 2-methoxyethylmethacrylate, 2-ethoxyethylmethacrylate, styrene, α-methylstyrene, acetoxystyrene, N-methylmaleimide, N-ethylmaleimide, N-propylmaleimide, N-butylmaleimide, N-cyclohexylmaleimide, methacrylamide and N-methyl methacrylamide.

Another example of the acrylic polymer having an acrylic unsaturated bond on the side chain is a copolymer formed by an addition reaction of carboxylic acid to an acrylic copolymer containing an epoxy group, and includes binder resin obtained at the temperature of from 40 to 180° C. by an addition reaction of an acrylic monomer containing carboxylic acid such as acrylic acid, methacrylic acid, itaconic acid, maleic acid and maleic acid monoalkyl ester to an acrylic copolymer containing an epoxy group obtained by copolymerization of an acrylic monomer containing an epoxy group such as glycidylacrylate, glycidyl methacrylate, 3,4-epoxybutylmethacrylate, 2,3-epoxycyclohexylmethacrylate and 3,4-epoxycyclohexyl methylmethacrylate and two or more types of monomers of alkylmethacrylate such as methylmethacrylate and hexylmethacrylate, cyclohexylmethacrylate, isobornylmethacrylate, adamantylmethacrylate, dicyclopentanylmethacrylate, dicyclopentenylmethacrylate, benzylmethacrylate, 2-methoxyethylmethacrylate, 2-ethoxyethylmethacrylate, styrene, α-methylstyrene, acetoxystyrene, N-methylmaleimide, N-ethylmaleimide, N-propylmaleimide, N-butylmaleimide, N-cyclohexyl maleimide, methacrylamide and N-methyl methacrylamide.

In the photoresist composition of the present disclosure, the polymerizable compound having an ethylenically unsaturated bond is crosslinked by photoreaction when forming a pattern and contributes to pattern formation, and when heated at high temperature, is crosslinked to impart chemical resistance and heat resistance.

The polymerizable compound having an ethylenically unsaturated bond may be present in 0.001 to 40 wt %, preferably 0.5 to 30 wt %, and more preferably 1 to 20 wt %, based on 100 wt % of the photoresist composition. When the polymerizable compound having an ethylenically unsaturated bond is present in excess, disadvantages are that the degree of crosslinking excessively increases and elasticity of the pattern reduces.

The polymerizable compound having an ethylenically unsaturated bond specifically includes alkylester of methacrylic acid such as methylmethacrylate, ethylmethacrylate, butylmethacrylate, 2-ethylhexylmethacrylate and laurylmethacrylate, glycidylmethacrylate, polyethylene glycolmonomethacrylate having 2 to 14 ethylene oxide groups, ethyleneglycoldimethacrylate, polyethylene glycol dimethacrylate having 2 to 14 ethylene oxide groups, propylene glycol dimethacrylate having 2 to 14 propylene oxide groups, trimethylolpropanedi methacrylate, bisphenol A diglycidyletheracrylic acid adducts, phthalic acid diester of β-hydroxy ethylmethacrylate, toluene diisocyanate adducts of β-hydroxyethylmethacrylate, compounds obtained by esterification of polyalcohol and α,β-unsaturated carboxylic acid, such as trimethylolpropanetrimethacrylate, pentaerythritoltrimethacrylate, pentaerythritoltetra methacrylate, dipentaerythritolpentamethacrylate, dipentaerythritolhexamethacrylate and dipentaerythritol trimethacrylate, and acrylic acid adducts of poly glycidyl compounds such as trimethylolpropanetriglycidyletheracrylic acid adducts, used singly or in combination.

Also, it is more effective to add the fluorenyl oxime ester compound used as the photopolymerization initiator in the photoresist composition of the present disclosure, in an amount of 0.01 to 10 wt %, preferably 0.1 to 5 wt %, and more preferably 0.5 to 3 wt % based on 100 wt % of the photoresist composition, which is the content for increasing transparency while minimizing the exposure dose.

The photoresist composition of the present disclosure is used to form a pattern through a method which adds a solvent, performs spin coating on a substrate, radiates ultraviolet rays using a mask, and develops using an alkali developer solution, and it is preferred to add the solvent in an amount of 10 to 95 wt %, preferably 20 to 50 wt %, and more preferably 25 to 45 wt %, based on 100 wt % of the photoresist composition, such that the viscosity is adjusted to range from 1 to 50 cps.

The solvent includes ethylacetate, butylacetate, diethyleneglycoldimethylether, diethyleneglycol dimethylethyether, methylmethoxy propionate, ethylethoxy propionate (EEP), ethyl lactate, propylene glycol monomethyl ether acetate (PGMEA), propylene glycol methyl ether propionate (PGMEP), propylene glycol methyl ether, propylene glycol propyl ether, methylcellosolveacetate, ethylcellosolveacetate, diethylene glycolmethylacetate, diethyleneglycolethylacetate, acetone, methylisobutyl ketone, cyclohexanone, dimethyl formamide (DMF), N,N-dimethyl acetamide (DMAc), N-methyl-2-pyrrolidone (NMP), γ-butyrolactone, diethylether, ethyleneglycol dimethyl ether, diglyme, tetrahydrofuran (THF), methanol, ethanol, propanol, iso-propanol, methylcellosolve, ethylcellosolve, diethyleneglycolmethyl ether, diethyleneglycolethylether, dipropylene glycol methyl ether, toluene, xylene, hexane, heptane, and octane, used singly or in combination, taking compatibility with the binder resin, the photoinitiator and the other compounds into account.

Also, the photoresist composition of the present disclosure may further include a silicone-based compound having an epoxy group or amine group as an auxiliary additive, if necessary.

In the photoresist composition, the silicone-based compound may improve the adhesion between an ITO electrode and the photoresist composition, and enhance heat resistance characteristics after curing. The silicone-based compound with an epoxy group or amine group includes (3-glycidoxypropyl)trimethoxysilane, (3-glycidoxypropyl)triethoxysilane, (3-glycidoxypropyl)methyldimethoxysilane, (3-glycidoxypropyl)methyldiethoxysilane, (3-glycidoxypropyl)dimethylmethoxysilane, (3-glycidoxypropyl)dimethylethoxysilane, 3,4-epoxybutyltrimethoxysilane, 3,4-epoxybutyltriethoxysilane, 2-(3,4-epoxycyclohexyl)ethyltrimethoxysilane, 2-(3,4-epoxycyclohexyl)ethyltriethoxysilane and aminopropyltrimethoxysilane, used singly or in combination. The silicone-based compound having an epoxy group or amine group may be present in 0.0001 to 3 parts by weight based on 100 parts by weight of the photoresist composition.

Also, the photoresist composition of the present disclosure may further include an additive having compatibility, such as a photo sensitizer a thermal polymerization inhibitor, an antifoaming agent, and a leveling agent, if necessary.

The photoresist composition according to an embodiment of the present disclosure is a known mean for a spin coater, a roll coater, a bar coater, a die coater, a curtain coater, and a wide range of printing and deposition applications, and may be applied to a support substrate such as a soda-lime glass, a quartz glass, a semiconductor substrate, metal, paper, and plastic. Also, after applying to a support substrate such as a film, it is possible to transfer to another support substrate, and there is no limitation on its application method.

The photoresist composition according to an embodiment of the present disclosure may be used for a wide range of applications such as photocurable paints or varnishes, photocurable adhesives, printed substrates, or color filter for color liquid crystal displays such as color TVs, PC monitors, mobile information terminals and digital cameras, electrode materials for plasma display panels, powder coating, printing inks, printed boards, adhesives, compositions for dental uses, gel coatings, photoresists for electronic engineering, electroplating resists, etching resists, liquid and dry films, soldering resists, resists for making color filter in a wide range of display applications or forming structures in manufacturing processes of plasma display panels, electroluminescent displays and LCDs, compositions for encapsulating electric and electronic components, magnetic recording materials, fine machine parts, waveguides, optical switches, plating masks, etching masks, color test systems, glass fiber cable coatings, screen printing stencils, materials for making three-dimensional objects by stereolithography, holographic recording materials, image recording materials, fine electronic circuits, decolorizing materials, decolorizing materials for image recording materials, decolorizing materials for image recording materials using microcapsules, photoresist materials for printed wiring boards, photoresist materials for UV and visible laser direct imaging systems, and photoresist materials or protective layers used to form dielectric layers in the sequential stack of printed circuit boards, and is not limited thereto.

Specifically, the photoresist composition according to an embodiment of the present disclosure may further include carbon black and can be used for a black matrix, and may further include a colorantand can be used for a color filter.

The coloring material included for resist applications used to form a color filter or a black matrix is the color mixing system of red, green, blue and brown, namely, cyan, magenta, yellow, and black pigments. The pigment includes C.I. Pigment Yellow 12, 13, 14, 17, 20, 24, 55, 83, 86, 93, 109, 110, 117, 125, 137, 139, 147, 148, 153, 154, 166, 168, C.I. Pigment Orange 36, 43, 51, 55, 59, 61, C.I. Pigment Red 9, 97, 122, 123, 149, 168, 177, 180, 192, 215, 216, 217, 220, 223, 224, 226, 227, 228, 240, C.I. Pigment Violet 19, 23, 29, 30, 37, 40, 50, C.I. Pigment Blue 15, 15:1, 15:4, 15:6, 22, 60, 64, C.I. Pigment Green 7, 36, C.I. Pigment Brown 23, 25, 26, C.I. Pigment Black 7, and Titan Black.

Hereinafter, a representative compound of the present disclosure will be described in detail through examples and comparative examples for the purpose of full understanding of the present disclosure, and the embodiments according to the present disclosure may be modified in many different forms, and the scope of the present disclosure shall not be construed as being limited to the embodiments mentioned below. The embodiments of the present disclosure are provided to describe the present disclosure more fully to those skilled in the art.

[Example 1] Preparation of 1-(9,9-diethyl-9H-fluorene-2-yl)-1,2-propanedione-2-oxime-O-acetate Reaction 1. Synthesis of 9,9-diethyl-9H-fluorene (2)

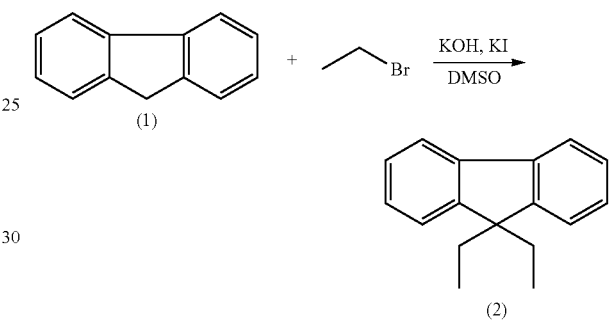

200.0 g (1.20 mol) fluorine(1), 268.8 g (4.80 mol) potassium hydroxide and 19.9 g (0.12 mol) potassium iodide were dissolved in 1 L anhydrous dimethylsulfoxide under nitrogen atmosphere, and after the reactants were maintained at 15° C., 283.3 g (2.60 mol) bromoethane was added slowly over 2 hours and the reactants were stirred at 15° C. for 1 hour. Subsequently, 2 L distilled water was added to the reactants, and after stirring for 30 minutes, a product was extracted with 2 L dichloromethane, and after the extracted organic layer was washed with 2 L distilled water twice, the recovered organic layer was dried with anhydrous magnesium sulfate and the solvent was distilled off under reduced pressure, and a resulting product is distilled by fractional distillation under reduced pressure to give 248.6 g (93.3%) 9,9-diethyl-9H-fluorene(2) in pale yellow as a liquid having high viscosity.

1H NMR (δ ppm; CDCl3): 0.31 (6H, t), 2.0 (4H, q), 7.26-7.31 (6H, m), 7.68 (2H, d)

MS (m/e): 222

Reaction 2. Synthesis of 1-(9,9-diethyl-9H-fluorene-2-yl)-1-propanone(3)

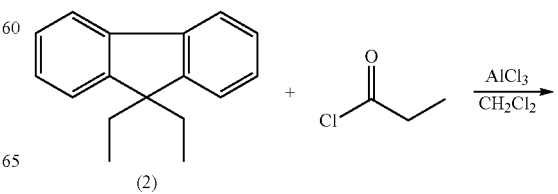

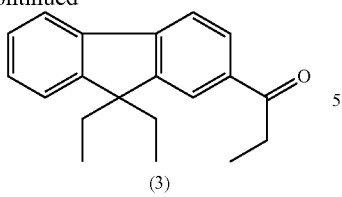

(3)

100.5 g (0.45 mol) 9,9-diethyl-9H-fluorene(2) was dissolved in 1 L dichloromethane, and after the reactants were cooled to −5° C., 72.3 g (0.54 mol) aluminum chloride was added slowly, 50.1 g (0.54 mol) propionyl chloride diluted with 50 ml dichloromethane was added slowly over 2 hours with care to avoid increasing the temperature of the reactants, and the reactants were stirred at −5° C. for 1 hour. Subsequently, the reactants were poured into 1 L ice water slowly and stirred for 30 minutes to separate an organic layer, followed by washing with 500 ml distilled water, the recovered organic layer was distilled under reduced pressure, and a resulting product was purified by silica gel column chromatography (eluting solvent; ethylacetate:n-hexane=1:4) to give 75.8 g (60.6%) 1-(9,9-diethyl-9H-fluorene-2-yl)-1-propanone(3) as a pale yellow solid.

1H NMR (δ ppm; CDCl3): 0.29 (6H, t), 1.28 (3H, t), 2.04 (4H, q), 3.06 (2H, q), 7.35-7.36 (3H, m), 7.75 (2H, t), 7.97 (2H, d)

MS (m/e): 278

Reaction 3. Synthesis of 1-(9,9-diethyl-9H-fluorene-2-yl)-1,2-propanedione-2-oxime(4)

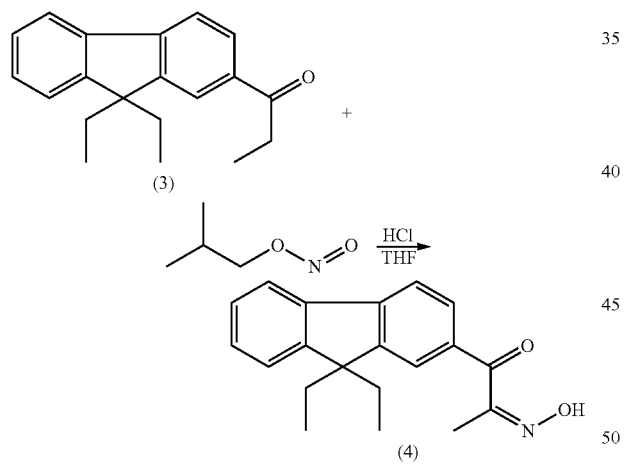

44.5 g (0.16 mol) 1-(9,9-diethyl-9H-fluorene-2-yl)-1-propanone(3) was dissolved in 900 ml tetrahydrofuran (THF), 150 ml 4N HCl and 24.7 g (0.24 mol) isobutyl nitrite dissolved in 1,4-dioxane were added in a sequential order, and the reactants were stirred at 25° C. for 6 hours. Subsequently, 500 ml ethylacetate was added to the reaction solution and stirred for 30 minutes to separate an organic layer, followed by washing with 600 ml distilled water, then the recovered organic layer was dried with anhydrous magnesium sulfate and the solvent was distilled off under reduced pressure, and a resulting solid product was re-crystallized using 300 ml a mixture solvent of ethylacetate:hexane (1:6) and dried to give 27.5 g (56.0%) 1-(9,9-diethyl-9H-fluorene-2-yl)-1,2-propanedione-2-oxime(4) as a pale grey solid.

1H NMR (δ ppm; CDCl3): 0.30 (6H, t), 2.06 (4H, q), 2.3 (3H, s), 7.26-7.37 (3H, m), 7.73 (2H, t), 7.97 (2H, d), 8.31 (1H, s)

MS (m/e): 307

Reaction 4. Synthesis of 1-(9,9-diethyl-9H-fluorene-2-yl)-1,2-propanedione-2-oxime-O-acetate(5)

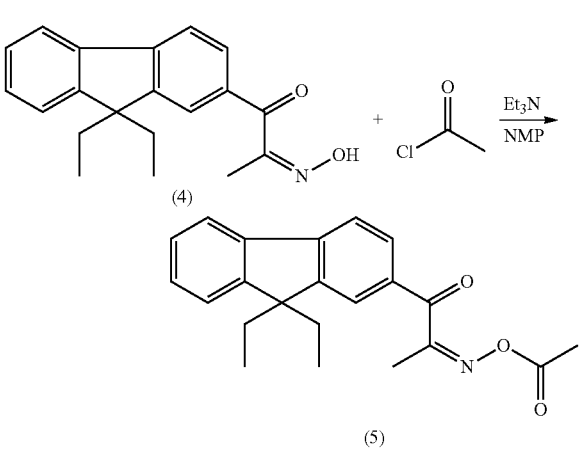

89.0 g (0.29 mol) 1-(9,9-diethyl-9H-fluorene-2-yl)-1,2-propanedione-2-oxime(4) was dissolved in 1 L N-methyl-2-pyrrolidinone (NMP) under nitrogen atmosphere, and after the reactants were maintained at −5° C., then 35.4 g (0.35 mol) trimethylamine was added, the reaction solution was stirred for 30 minutes, and a solution of 27.5 g (0.35 mol) acetyl chloride dissolved in 75 ml N-methyl-2-pyrrolidinone was added slowly over 30 minutes and stirred for 30 minutes with care to avoid increasing the temperature of the reactants. Subsequently, 1 L distilled water was added to the reactants slowly and stirred for 30 minutes to separate an organic layer, and the recovered organic layer was dried with anhydrous magnesium sulfate and the solvent was distilled off under reduced pressure. A resulting solid product was re-crystallized using 1 L ethanol and dried to give 93.7 g (92.6%) 1-(9,9-diethyl-9H-fluorene-2-yl)-1,2-propanedione-2-oxime-O-acetate(5) as a pale grey solid.

1H NMR (δ ppm; CDCl3): 0.31 (6H, t), 2.08 (4H, q), 2.29 (3H, s), 2.33 (3H, s), 7.36-7.38 (3H, m), 7.76 (2H, t), 8.12 (2H, d)

MS (m/e): 349

[Example 2] Preparation of 1-(9,9-diethyl-9H-fluorene-2-yl)-1,2-propanedione-2-oxime-O-propylate (6)

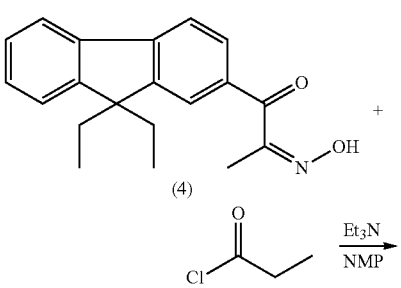

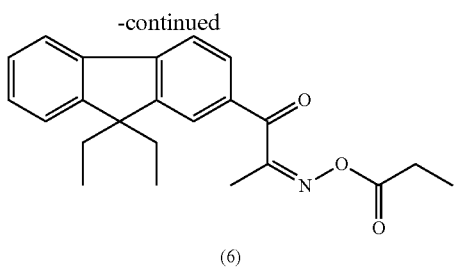

(6)

89.0 g (0.29 mol) 1-(9,9-diethyl-9H-fluorene-2-yl)-1,2-propanedione-2-oxime(4) was dissolved in 1 L N-methyl-2-pyrrolidinone (NMP) under nitrogen atmosphere, and after the reactants were maintained at −5° C., then 35.4 g (0.35 mol) triethylamine was added, the reaction solution was stirred for 30 minutes, and a solution of 32.4 g (0.35 mol) propionyl chloride dissolved in 75 ml N-methyl-2-pyrrolidinone was added slowly over 30 minutes and stirred for 30 minutes with care to avoid increasing the temperature of the reactants. Subsequently, 1 L distilled water was added to the reactants slowly and stirred for 30 minutes to separate an organic layer, and the recovered organic layer was dried with anhydrous magnesium sulfate and the solvent was distilled off under reduced pressure. A resulting solid product was re-crystalized using 1 L ethanol and dried to give 95.9 g (91.1%) 1-(9,9-diethyl-9H-fluorene-2-yl)-1,2-propanedione-2-oxime-O-propylate(6) as a pale grey solid.

1H NMR (δ ppm; CDCl3): 0.32 (6H, t), 1.03 (3H, t), 1.78 (2H, q), 2.05 (4H, q), 2.33 (3H, s), 2.55 (2H, q), 7.36-7.38 (3H, m), 7.79 (2H, t), 8.15 (2H, d)

MS (m/e): 363

[Example 3] Preparation of 1-(9,9-diethyl-9H-fluorene-2-yl)-1,2-propanedione-2-oxime-O-butylate(7)

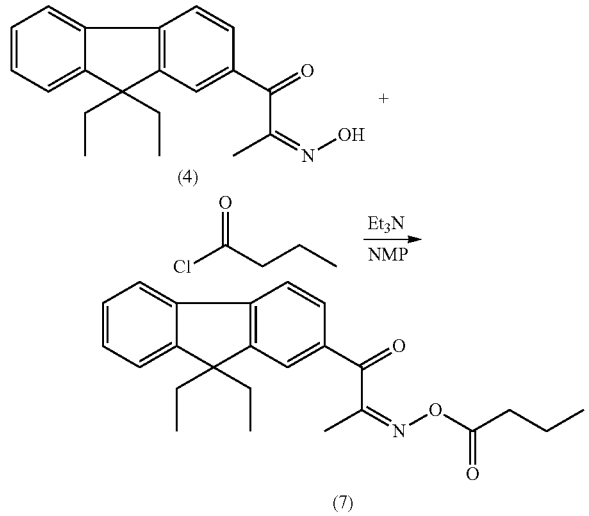

29.8 g (0.097 mol) 1-(9,9-diethyl-9H-fluorene-2-yl)-1,2-propanedione-2-oxime(4) was dissolved in 300 ml N-methyl-2-pyrrolidinone (NMP) under nitrogen atmosphere, and after the reactants were maintained at −5° C., then 11.7 g (0.116 mol) triethylamine was added, the reaction solution was stirred for 30 minutes, and a solution of 12.4 g (0.116 mol) butyryl chloride dissolved in 15 ml N-methyl-2-pyrrolidinone was added slowly over 30 minutes and stirred for 30 minutes with care to avoid increasing the temperature of the reactants. Subsequently, after 300 ml distilled water was added to the reactants slowly and stirred for 30 minutes to separate an organic layer, the recovered organic layer was dried with anhydrous magnesium sulfate and the solvent was distilled off under reduced pressure, and a resulting product was purified by silica gel column chromatography (eluting solvent; ethylacetate:n-hexane=1:4) to give 32.9 g (90.0%) 1-(9,9-diethyl-9H-fluorene-2-yl)-1,2-propanedione-2-oxime-O-butylate(7).

1H NMR (δ ppm; CDCl3): 0.32 (6H, t), 0.94 (3H, t), 1.78 (2H, q), 2.08 (4H, m), 2.10 (3H, s), 2.55 (2H, t), 7.35-7.38 (3H, m), 7.78 (2H, t), 8.15 (2H, d)

MS (m/e): 377

[Example 4] Preparation of 1-(9,9-diethyl-9H-fluorene-2-yl)-1,2-propanedione-2-oxime-O-valerate(8)

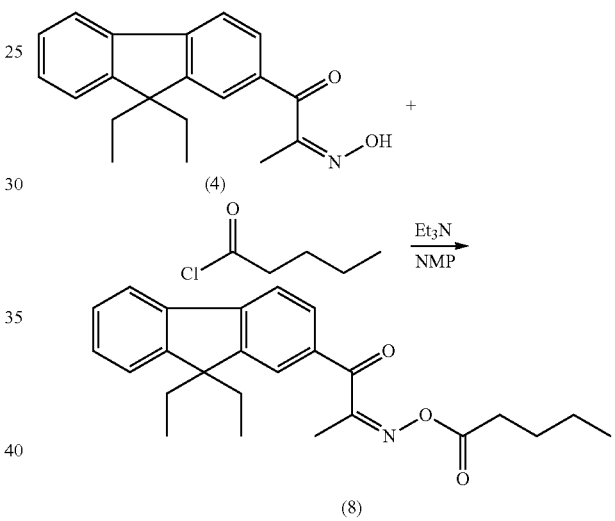

89.0 g (0.29 mol) 1-(9,9-diethyl-9H-fluorene-2-yl)-1,2-propanedione-2-oxime(4) was dissolved in 1 L N-methyl-2-pyrrolidinone (NMP) under nitrogen atmosphere, and after the reactants were maintained at −5° C., then 35.4 g (0.35 mol) triethylamine was added, the reaction solution was stirred for 30 minutes, and a solution of 42.2 g (0.35 mol) valeryl chloride dissolved in 75 ml N-methyl-2-pyrrolidinone was added slowly over 30 minutes and stirred for 30 minutes with care to avoid increasing the temperature of the reactants. Subsequently, after 1 L distilled water was added to the reactants slowly and stirred for 30 minutes to separate an organic layer, the recovered organic layer was dried with anhydrous magnesium sulfate and the solvent was distilled off under reduced pressure, and a resulting product was purified by silica gel column chromatography (eluting solvent; ethylacetate:n-hexane=1:4) to give 100.0 g (88.2%) 1-(9,9-diethyl-9H-fluorene-2-yl)-1,2-propanedione-2-oxime-O-valerate(8).

1H NMR (δ ppm; CDCl3): 0.32 (6H, t), 0.94 (3H, t), 1.55 (2H, m), 1.78 (2H, m), 2.08 (4H, q), 2.10 (3H, s), 2.55 (2H, t), 7.35-7.38 (3H, m), 7.78 (2H, t), 8.15 (2H, d)

MS (m/e): 391

[Example 5] Preparation of 1-(9,9-diethyl-9H-fluorene-2-yl)-1,2-propanedione-2-oxime-O-hexylate(9)

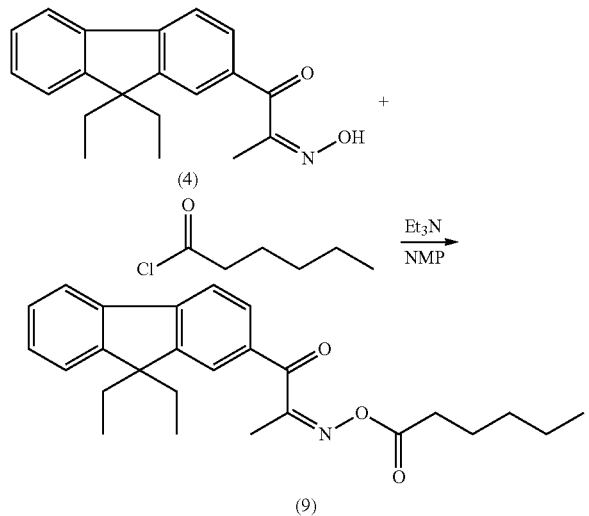

89.0 g (0.29 mol) 1-(9,9-diethyl-9H-fluorene-2-yl)-1,2-propanedione-2-oxime(4) was dissolved in 1 L N-methyl-2-pyrrolidinone (NMP) under nitrogen atmosphere, and after the reactants were maintained at −5° C., then 35.4 g (0.35 mol) triethylamine was added, the reaction solution was stirred for 30 minutes, and a solution of 47.1 g (0.35 mol) hexanoyl chloride dissolved in 75 ml N-methyl-2-pyrrolidinone was added slowly over 30 minutes and stirred for 30 minutes with care to avoid increasing the temperature of the reactants. Subsequently, after 1 L distilled water was added to the reactants slowly and stirred for 30 minutes to separate an organic layer, the recovered organic layer was dried with anhydrous magnesium sulfate and the solvent was distilled off under reduced pressure, and a resulting product was purified by silica gel column chromatography (eluting solvent; ethylacetate:n-hexane=1:4) to give 105.8 g (90.1%) 1-(9,9-diethyl-9H-fluorene-2-yl)-1,2-propanedione-2-oxime-O-hexylate(9).

1H NMR (δ ppm; CDCl3): 0.32 (6H, t), 0.92 (3H, t), 1.35 (4H, m), 1.78 (2H, m), 2.05 (4H, q), 2.10 (3H, s), 2.55 (2H, t), 7.35-7.38 (3H, m), 7.78 (2H, t), 8.15 (2H, d)

MS (m/e): 405

[Example 6] Preparation of 1-(9,9-diethyl-9H-fluorene-2-yl)-1,2-propanedione-2-oxime-O-heptylate (10)

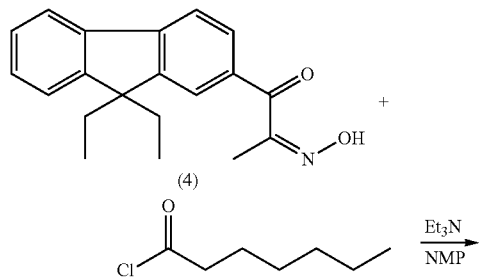

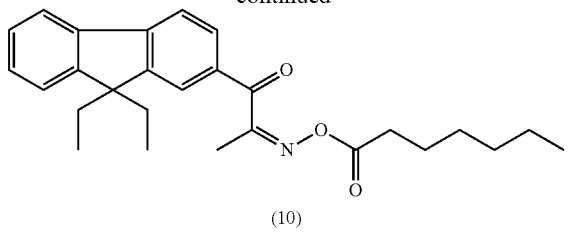

89.0 g (0.29 mol) 1-(9,9-diethyl-9H-fluorene-2-yl)-1,2-propanedione-2-oxime(4) was dissolved in 1 L N-methyl-2-pyrrolidinone (NMP) under nitrogen atmosphere, and after the reactants were maintained at −5° C., then 35.4 g (0.35 mol) triethylamine was added, the reaction solution was stirred for 30 minutes, and a solution of 52.0 g (0.35 mol) heptanoyl chloride dissolved in 75 ml N-methyl-2-pyrrolidinone was added slowly over 30 minutes and stirred for 30 minutes with care to avoid increasing the temperature of the reactants. Subsequently, after 1 L distilled water was added to the reactants slowly and stirred for 30 minutes to separate an organic layer, the recovered organic layer was dried with anhydrous magnesium sulfate and the solvent was distilled off under reduced pressure, and a resulting product was purified by silica gel column chromatography (eluting solvent; ethylacetate:n-hexane=1:4) to give 111.9 g (92.1%) 1-(9,9-diethyl-9H-fluorene-2-yl)-1,2-propanedione-2-oxime-O-heptylate(10).

1H NMR (δ ppm; CDCl3): 0.32 (6H, t), 0.88 (3H, t), 1.33 (6H, m), 1.88 (2H, m), 2.03 (4H, q), 2.07 (3H, s), 2.55 (2H, t), 7.35-7.38 (3H, m), 7.79 (2H, t), 8.16 (2H, d)

MS (m/e): 419

[Example 7] Preparation of 1-(9,9-dibutyl-9H-fluorene-2-yl)-1,2-propanedione-2-oxime-O-acetate(14)

Reaction 1. Synthesis of 9,9-dibutyl-9H-fluorene(11)

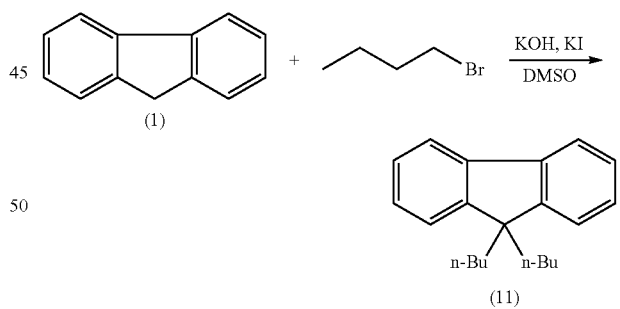

100.0 g (0.60 mol) fluorene(1), 134.4 g (2.4 mol) potassium hydroxide and 9.96 g (0.06 mol) potassium iodide were dissolved in 500 ml anhydrous dimethylsulfoxide under nitrogen atmosphere, and after the reactants were maintained at 15° C., 182.2 g (1.33 mol) bromobutane was added slowly over 2 hours and the reactants were stirred at 15° C. for 1 hour. Subsequently, after 2 L distilled water was added to the reactants and stirred for about 30 minutes, a product was extracted with 2 L dichloromethane and the extracted organic layer was washed with 2 L distilled water twice, then the recovered organic layer was dried with anhydrous magnesium sulfate and the solvent was distilled off under reduced pressure, and a resulting product was purified by silica gel column chromatography (eluting solvent; ethylacetate:n-hexane=1:20) to give 147.8 g (88.5%) 9,9-dibutyl-9H-fluorene(11) as a white solid.

1H NMR (δ ppm; CDCl3): 0.60 (4H, m), 0.64 (6H, t), 1.08 (4H, m), 1.95 (4H, t), 7.30-7.34 (6H, m), 7.71 (2H, d)

MS (m/e): 278

Reaction 2. Synthesis of 1-(9,9-dibutyl-9H-fluorene-2-yl)propan-1-one(12)

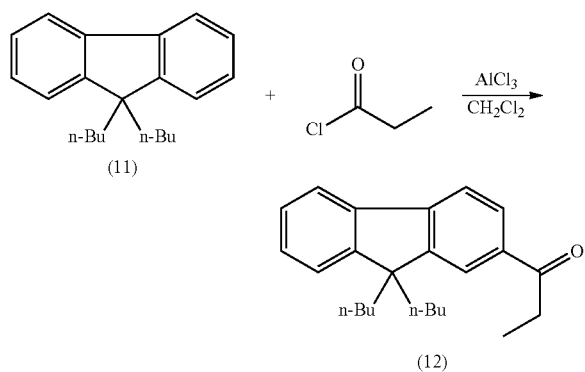

30.6 g (0.11 mol) 9,9-dibutyl-9H-fluorene(11) was dissolved in 500 ml dichloromethane and after cooling to −5° C., 17.6 g (0.13 mol) aluminum chloride was added slowly, and 12.0 g (0.13 mol) propionyl chloride diluted with 15 ml dichloromethane was dropped slowly over 1 hour with care to avoid increasing the temperature of the reactants and stirred at −5° C. for 1 hour. Subsequently, the reactants were poured into 500 ml ice water slowly and stirred for 30 minutes, and after an organic layer was washed with 200 mL distilled water, a product obtained by distilling the recovered organic layer under reduced pressure was purified by silica gel column chromatography (eluting solvent; ethylacetate:n-hexane=1:4) to give 22.1 g (60.2%) 1-(9,9-dibutyl-9H-fluorene-2-yl)propan-1-one(12).

1H NMR (δ ppm; CDCl3): 0.55 (4H, m), 0.65 (6H, t), 1.07 (4H, m), 1.25 (3H, t), 1.99 (4H, t), 3.09 (2H, q), 7.36-7.37 (3H, d), 7.75 (2H, d), 7.97 (2H, d)

MS (m/e): 334

Reaction 3. Synthesis of 1-(9,9-dibutyl-9H-fluorene-2-yl)-1,2-propanedione-2-oxime(13)

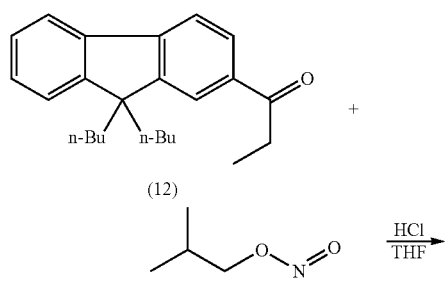

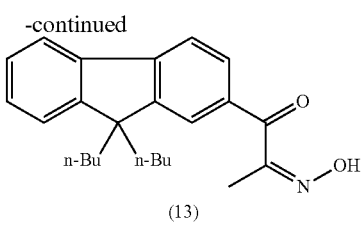

14.0 g (0.042 mol) 1-(9,9-dibutyl-9H-fluorene-2-yl)propan-1-one(12) was dissolved in 200 ml tetrahydrofuran (THF), 25 ml 4N HCl and 6.5 g (0.063 mol) isobutyl nitrite dissolved in 1,4-dioxane were added in a sequential order, and the reactants were stirred at 25° C. for 6 hours. Subsequently, 200 ml ethylacetate was added to the reaction solution and stirred for 30 minutes to separate an organic layer, followed by washing with 200 ml distilled water, then the recovered organic layer was dried with anhydrous magnesium sulfate and the solvent was distilled off under reduced pressure, and a resulting product was purified by silica gel column chromatography (eluting solvent; ethylacetate:n-hexane=1:4) to give 7.94 g (52.1%) 1-(9,9-dibutyl-9H-fluorene-2-yl)-1,2-propanedione-2-oxime(13).

1H NMR (δ ppm; CDCl3): 0.59 (4H, m), 0.65 (6H, t), 1.07 (4H, m), 1.98 (4H, q), 2.21 (3H, s), 7.36-7.38 (3H, d), 7.75 (2H, d), 7.96 (2H, d), 8.30 (1H, s)

MS (m/e): 363

Reaction 4. Synthesis of 1-(9,9-dibutyl-9H-fluorene-2-yl)-1,2-propanedione-2-oxime-O-acetate(14)

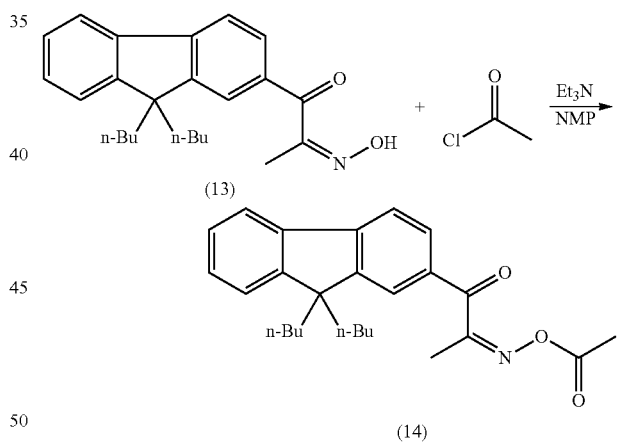

20.5 g (0.056 mol) 1-(9,9-dibutyl-9H-fluorene-2-yl)-1,2-propanedione-2-oxime(11) was dissolved in 200 ml N-methyl-2-pyrrolidinone (NMP) under nitrogen atmosphere, and after the reactants were maintained at −5° C., then 6.87 g (0.068 mol) triethylamine was added, the reaction solution was stirred for 30 minutes, and a solution of 5.34 g (0.068 mol) acetyl chloride dissolved in 10 ml N-methyl-2-pyrrolidinone was added slowly over 30 minutes and stirred for 30 minutes with care to avoid increasing the temperature of the reactants. Subsequently, after 200 ml distilled water was added to the reactants slowly and stirred for 30 minutes to separate an organic layer, the recovered organic layer was dried with anhydrous magnesium sulfate and the solvent was distilled off under reduced pressure, and a resulting solid product was re-crystallized using 1 L ethanol and dried to give 20.1 g (88.6%) 1-(9,9-dibutyl-9H-fluorene-2-yl)-1,2-propanedione-2-oxime-O-acetate(14).

1H NMR (δ ppm; CDCl3): 0.58 (4H, m), 0.66 (6H, t), 1.06 (4H, m), 2.00 (4H, t), 2.29 (3H, s), 2.34 (3H, s), 7.36-7.38 (3H, d), 7.77 (2H, d), 8.11 (2H, d)

MS (m/e): 405

[Example 8] Preparation of 1-(9,9-dibutyl-9H-fluorene-2-yl)-1,2-propanedione-2-oxime-O-propylate (15)

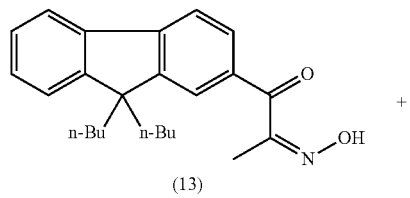

(13)

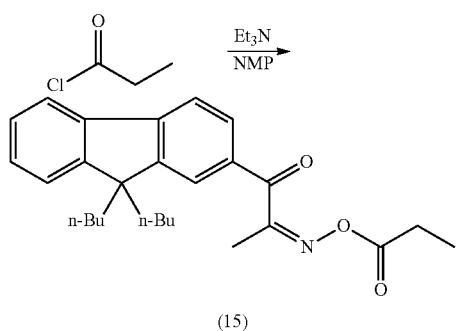

(15)

20.5 g (0.056 mol) 1-(9,9-dibutyl-9H-fluorene-2-yl)-1,2-propanedione-2-oxime(13) was dissolved in 200 ml N-methyl-2-pyrrolidinone(NMP) under nitrogen atmosphere, and after the reactants were maintained at −5° C., then 6.87 g (0.068 mol) triethylamine was added, the reaction solution was stirred for 30 minutes, a solution of 6.29 g (0.068 mol) propionyl chloride dissolved in 10 ml N-methyl-2-pyrrolidinone was added slowly over 30 minutes and stirred for 30 minutes with care to avoid increasing the temperature of the reactants. Subsequently, after 200 ml distilled water was added to the reactants slowly and stirred for 30 minutes to separate an organic layer, the recovered organic layer was dried with anhydrous magnesium sulfate and the solvent was distilled off under reduced pressure, and a resulting product was purified by silica gel column chromatography (eluting solvent; ethylacetate:n-hexane=1:4) to give 20.7 g (88.2%) 1-(9,9-dibutyl-9H-fluorene-2-yl)-1,2-propanedione-2-oxime-O-propylate(15).

1H NMR (δ ppm; CDCl3): 0.58 (4H, m), 0.66 (6H, t), 0.99 (3H, t), 1.06 (4H, m), 1.78 (2H, t), 2.00 (4H, t), 2.34 (3H, s), 7.36-7.38 (3H, d), 7.75 (2H, d), 8.13 (2H, d)

MS (m/e): 419

[Example 9] Preparation of 1-(9,9-dibutyl-9H-fluorene-2-yl)-1,2-propanedione-2-oxime-O-butylate(16)

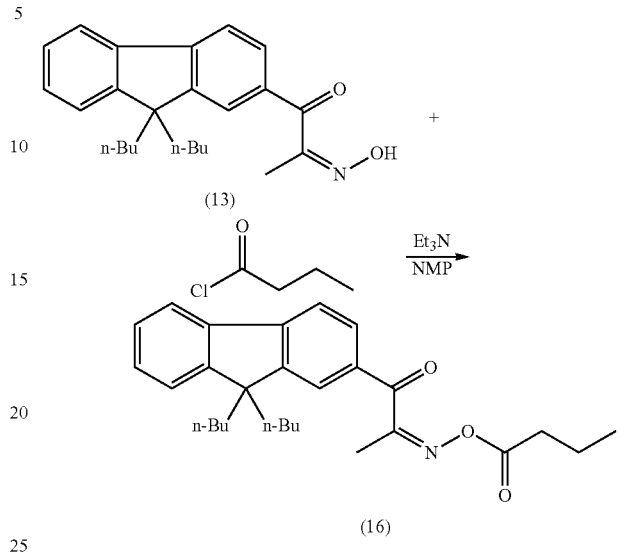

(13)

(16)

20.5 g (0.056 mol) 1-(9,9-dibutyl-9H-fluorene-2-yl)-1,2-propanedione-2-oxime(13) was dissolved in 200 ml N-methyl-2-pyrrolidinone (NMP) under nitrogen atmosphere, and after the reactants were maintained at −5° C., then 6.87 g (0.068 mol) triethylamine was added, the reaction solution was stirred for 30 minutes, and a solution of 7.25 g (0.068 mol) butyryl chloride dissolved in 10 ml N-methyl-2-pyrrolidinone was added slowly over 30 minutes and stirred for 30 minutes with care to avoid increasing the temperature of the reactants. Subsequently, after 200 ml distilled water was added to the reactants slowly and stirred for 30 minutes to separate an organic layer, the recovered organic layer was dried with anhydrous magnesium sulfate and the solvent was distilled off under reduced pressure, and a resulting product was purified by silica gel column chromatography (eluting solvent; ethylacetate:n-hexane=1:4) to give 21.6 g (89.0%) 1-(9,9-dibutyl-9H-fluorene-2-yl)-1,2-propanedione-2-oxime-O-butylate(16).

1H NMR (δ ppm; CDCl3): 0.58 (4H, m), 0.66 (6H, t), 0.97 (3H, t), 1.06 (4H, m), 1.55 (2H, m), 1.78 (2H, t), 2.00 (4H, t), 2.33 (3H, s), 7.36-7.38 (3H, d), 7.75 (2H, d), 8.12 (2H, d)

MS (m/e): 433

[Example 10] Preparation of 1-(9,9-dibutyl-9H-fluorene-2-yl)-1,2-propanedione-2-oxime-O-valerate (17)

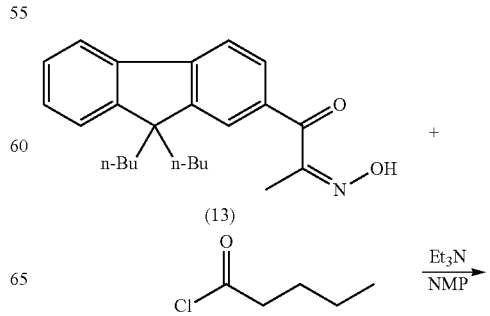

(13)

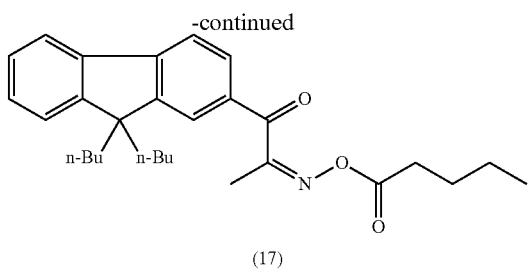

(17)

20.5 g (0.056 mol) 1-(9,9-dibutyl-9H-fluorene-2-yl)-1,2-propanedione-2-oxime(13) was dissolved in 200 ml N-methyl-2-pyrrolidinone (NMP) under nitrogen atmosphere, and after the reactants were maintained at −5° C., then 6.87 g (0.068 mol) triethylamine was added, the reaction solution was stirred for 30 minutes, and a solution of 8.20 g (0.068 mol) valeryl chloride dissolved in 10 ml N-methyl-2-pyrrolidinone was added slowly over 30 minutes and stirred for 30 minutes with care to avoid increasing the temperature of the reactants. Subsequently, after 200 ml distilled water was added to the reactants slowly and stirred for 30 minutes to separate an organic layer, the recovered organic layer was dried with anhydrous magnesium sulfate and the solvent was distilled off under reduced pressure, and a resulting product was purified by silica gel column chromatography (eluting solvent; ethylacetate:n-hexane=1:4) to give 22.6 g (90.3%) 1-(9,9-dibutyl-9H-fluorene-2-yl)-1,2-propanedione-2-oxime-O-valerate(17).

1H NMR (δ ppm; CDCl3): 0.55 (4H, m), 0.64 (6H, t), 0.95 (3H, t), 1.06 (4H, m), 1.55 (2H, m), 1.78 (2H, q), 2.00 (4H, t), 2.08 (2H, m), 2.33 (3H, s), 7.36-7.38 (3H, d), 7.75 (2H, d), 8.14 (2H, d))

MS (m/e): 447

[Example 11] Preparation of 1-(9,9-dibutyl-9H-fluorene-2-yl)-1,2-propanedione-2-oxime-O-hexylate(18)

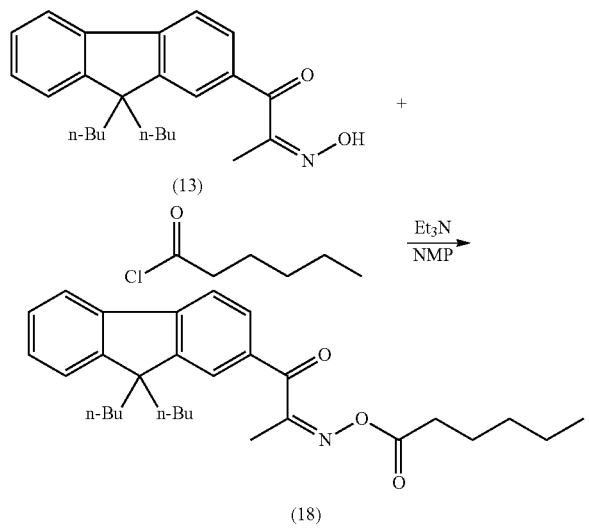

20.5 g (0.056 mol) 1-(9,9-dibutyl-9H-fluorene-2-yl)-1,2-propanedione-2-oxime(13) was dissolved in 200 ml N-methyl-2-pyrrolidinone (NMP) under nitrogen atmosphere, and after the reactants were maintained at −5° C., then 6.87 g (0.068 mol) triethylamine was added, the reaction solution was stirred for 30 minutes, and a solution of 9.15 g (0.068 mol) hexanoyl chloride dissolved in 10 ml N-methyl-2-pyrrolidinone was added slowly over 30 minutes and stirred for 30 minutes with care to avoid increasing the temperature of the reactants. Subsequently, after 200 ml distilled water was added to the reactants slowly and stirred for 30 minutes to separate an organic layer, the recovered organic layer was dried with anhydrous magnesium sulfate and the solvent was distilled off under reduced pressure, and a resulting product was purified by silica gel column chromatography (eluting solvent; ethylacetate:n-hexane=1:4) to give 22.8 g (88.1%) 1-(9,9-dibutyl-9H-fluorene-2-yl)-1,2-propanedione-2-oxime-O-hexylate(18).

1H NMR (δ ppm; CDCl3): 0.55 (4H, m), 0.64 (6H, t), 0.95 (3H, t), 1.06 (4H, m), 1.55 (2H, m), 1.78 (2H, t), 2.00 (4H, t), 2.08 (2H, m), 2.33 (3H, s), 2.57 (2H, t), 7.36-7.38 (3H, d), 7.75 (2H, d), 8.14 (2H, d)

MS (m/e): 461

[Example 12] Preparation of 1-(9,9-dibutyl-9H-fluorene-2-yl)-1,2-propanedione-2-oxime-O-heptylate(19)

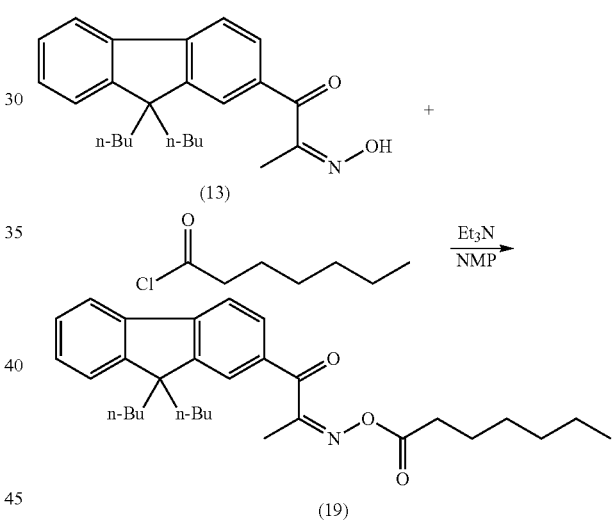

20.5 g (0.056 mol) 1-(9,9-dibutyl-9H-fluorene-2-yl)-1,2-propanedione-2-oxime(13) was dissolved in 200 ml N-methyl-2-pyrrolidinone (NMP) under nitrogen atmosphere, and after the reactants were maintained at −5° C., then 6.87 g (0.068 mol) triethylamine was added, the reaction solution was stirred for 30 minutes, and a solution of 10.1 g (0.068 mol) heptanoyl chloride dissolved in 10 ml N-methyl-2-pyrrolidinone was added slowly over 30 minutes and stirred for 30 minutes with care to avoid increasing the temperature of the reactants. Subsequently, after 200 ml distilled water was added to the reactants slowly and stirred for 30 minutes to separate an organic layer, the recovered organic layer was dried with anhydrous magnesium sulfate and the solvent was distilled off under reduced pressure, and a resulting product was purified by silica gel column chromatography (eluting solvent; ethylacetate:n-hexane=1:4) to give 22.7 g (85.3%) 1-(9,9-dibutyl-9H-fluorene-2-yl)-1,2-propanedione-2-oxime-O-heptylate(19).

1H NMR (δ ppm; CDCl3): 0.55 (4H, m), 0.64 (6H, t), 0.95 (3H, t), 1.33 (6H, m), 1.55 (2H, m), 1.78 (2H, t), 2.01

(4H, t), 2.08 (4H, m), 2.33 (3H, s), 2.57 (2H, t), 7.36-7.38 (3H, d), 7.75 (2H, d), 8.14 (2H, d)

MS (m/e): 475

[Example 13] Preparation of 1-(9,9-dimethyl-9H-fluorene-2-yl)-1,2-propanedione-2-oxime-O-acetate (23)

Reaction 1. Synthesis of 9,9-dimethyl-9H-fluorene(20)

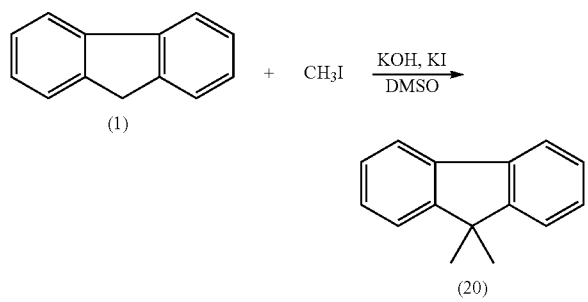

24.9 g (0.15 mol) fluorene(1), 42.0 g (0.75 mol) potassium hydroxide and 2.50 g (0.015 mol) potassium iodide were dissolved in 300 ml anhydrous dimethylsulfoxide under nitrogen atmosphere, and after the temperature of the reactants was raised to 70° C., 55.4 g (0.390 mol) iodomethane was added slowly over 4 hours with care to maintain the temperature of the reactants between 70~75° C. and stirred at 70° C. for 2 hours. Subsequently, the reactants were cooled to room temperature, 500 ml distilled water and 400 ml dichloromethane were added to extract a product, and after the extracted organic layer was washed with 400 ml distilled water twice, the recovered organic layer was dried with anhydrous magnesium sulfate and distilled under reduced pressure, and a resulting solid product was purified with 50 ml methanol twice and dried to give 22.1 g (75.9%) 9,9-dimethyl-9H-fluorene(20) in white.

1H NMR (δ ppm; CDCl3): 1.49 (6H, s), 7.29-7.36 (4H, m), 7.43-7.45 (2H, m), 7.72-7.74 (2H, m)

MS (m/e): 194

Reaction 2. Synthesis of 1-(9,9-dimethyl-9H-fluorene-2-yl)propan-1-one(21)

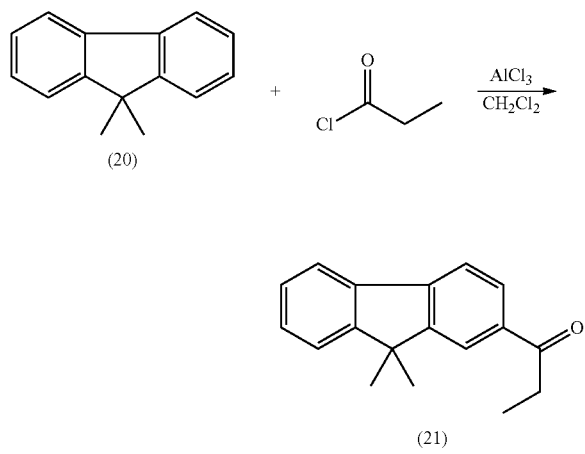

11.65 g (0.06 mol) 9,9-dimethyl-9H-fluorene(20) was dissolved in 90 ml dichloromethane, and after the reactants were cooled to −5° C., then 8.8 g (0.066 mol) anhydrous aluminum chloride was added, 6.1 g (0.066 mol) propionyl chloride diluted with 18 ml dichloromethane was added slowly over 1 hour with care to avoid increasing the temperature of the reactants and stirred at −5° C. for 1 hour. Subsequently, after the reactants were poured into 250 g ice water slowly and stirred for 30 minutes, an organic layer was separated and washed with 100 ml distilled water, and a solid product obtained by distillation of the recovered organic layer under reduced pressure was re-crystallized with 40 ml a mixed solution of ethanol:ethylacetate (7:1) to give 10.5 g (70.0%) 1-(9,9-diethyl-9H-fluorene-2-yl)propan-1-one (21) in pale yellow.

1H NMR (δ ppm; CDCl3): 1.23 (3H, t), 1.50 (6H, s), 3.03 (2H, q), 7.35-7.46 (3H, m), 7.74-7.76 (2H, m), 7.95 (1H, d), 8.04 (1H, s)

MS (m/e): 250

Reaction 3. Synthesis of 1-(9,9-dimethyl-9H-fluorene-2-yl)-1,2-propanedione-2-oxime(22)

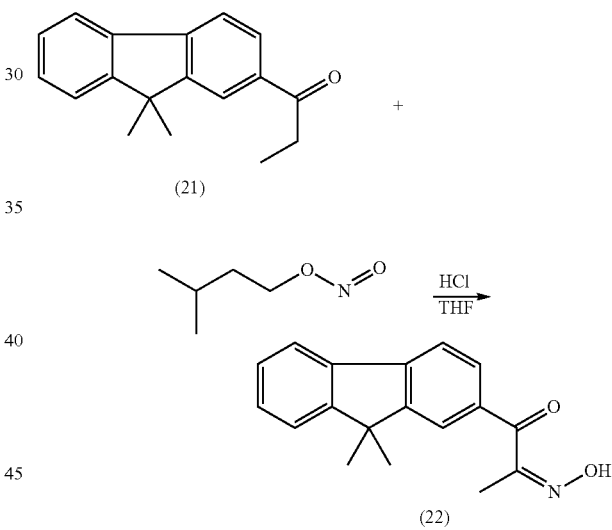

9.0 g (0.036 mol) 1-(9,9-dimethyl-9H-fluorene-2-yl)propan-1-one(21) was dissolved in 60 ml tetrahydrofuran (THF), 4N HCl 20 ml and 5.05 g (0.043 mol) isopentyl nitrite dissolved in 1,4-dioxane were added in a sequential order, and the reactants were stirred at 25° C. for 1 hour. Subsequently, after 20 ml ethylacetate was added to the reaction solution and washed with 100 ml distilled water, the recovered organic layer was dried with anhydrous magnesium sulfate and the solvent was distilled off under reduced pressure, and a resulting solid product was re-crystallized using 30 mL a mixed solvent of ethanol:ethylacetate (5:1) and dried to give 7.7 g (76.7%) 1-(9,9-dimethyl-9H-fluorene-2-yl)-1,2-propanedione-2-oxime(22) in pale grey.

1H NMR (δ ppm; CDCl3): 1.49 (6H, s), 2.17 (3H, s), 7.34-7.46 (3H, m), 7.73 (2H, t), 7.92 (1H, d), 7.98 (1H, s), 8.30 (1H, s)

MS (m/e): 279

Reaction 4. Synthesis of 1-(9,9-dimethyl-9H-fluorene-2-yl)-1,2-propanedione-2-oxime-O-acetate(23)

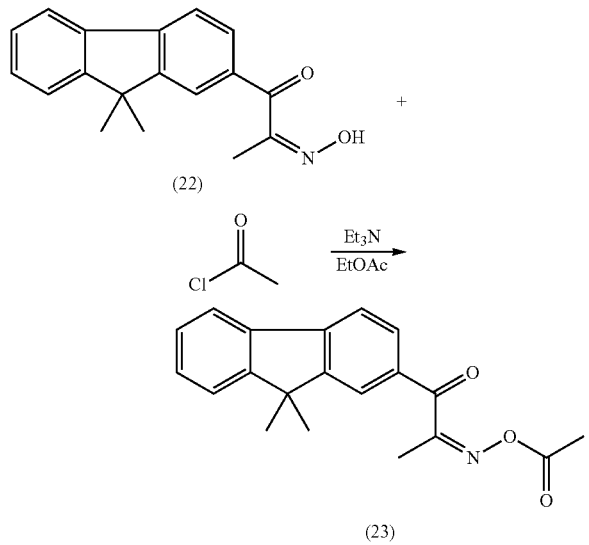

5.30 g (0.019 mol) 1-(9,9-dimethyl-9H-fluorene-2-yl)-1,2-propanedione-2-oxime(22) was dissolved in 75 ml ethylacetate under nitrogen atmosphere, and after the reactants were maintained at −5° C., then 2.36 g (0.023 mol) triethylamine was added, the reaction solution was stirred for 30 minutes, and a solution of 1.81 g (0.023 mol) acetyl chloride dissolved in 15 ml ethylacetate was added slowly over 30 minutes with care to avoid increasing the temperature of the reactants and stirred for 30 minutes. Subsequently, after 100 ml distilled water was added to the reactants slowly and stirred for 30 minutes, an organic layer was extracted, then the extracted organic layer was dried with anhydrous magnesium sulfate, and the solvent was distilled off under reduced pressure to give 5.8 g (95.1%) 1-(9,9-dimethyl-9H-fluorene-2-yl)-1,2-propanedione-2-oxime-O-acetate(23) in pale yellow as a liquid having high viscosity.

1H NMR (δ ppm; CDCl3): 1.50 (6H, s), 2.27 (3H, s), 2.32 (3H, s), 7.34 (2H, q), 7.44 (1H, d), 7.76 (2H, d), 8.07 (1H, d), 8.19 (1H, s)

MS (m/e): 321

[Example 14] Preparation of 1-(9H-fluorene-2-yl)-1,2-propanedione-2-oxime-O-acetate(26)

Reaction 1. Reaction 2. Synthesis of 1-(9H-fluorene-2-yl)propan-1-one(24)

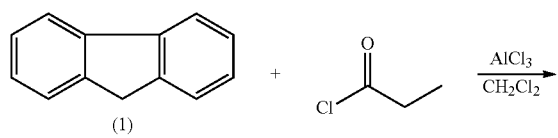

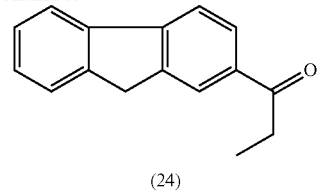

(24)

After 4.98 g (0.030 mol) fluorene (1) was dissolved in 45 ml dichloromethane, the reactants were cooled to −5° C., then 4.40 g (0.033 mol) anhydrous aluminum chloride was added, and 3.05 g (0.033 mol) propionyl chloride diluted with 9 ml dichloromethane was added slowly over 1 hour with care to avoid increasing the temperature of the reactants and stirred at −5° C. for 1 hour. Subsequently, after the reactants were poured into 250 g ice water slowly and stirred for 30 minutes, an organic layer was separated and washed with 100 ml distilled water, then the recovered organic layer was distilled under reduced pressure, and a resulting solid product was re-crystallized with 20 ml a mixed solution of toluene:ethylacetate (5:1) to give 2.5 g (37.5%) 1-(9H-fluorene-2-yl)propan-1-one (24) in pale grey.

1H NMR (δ ppm; DMSO-d6): 1.08 (3H, t), 3.06 (2H, q), 3.99 (2H, s), 7.37-7.44 (2H, m), 7.62 (1H, d), 7.99-8.01 (3H, m), 8.17 (1H, s)

MS (m/e): 222

Reaction 2. Synthesis of 1-(9H-fluorene-2-yl)-1,2-propanedione-2-oxime(25)

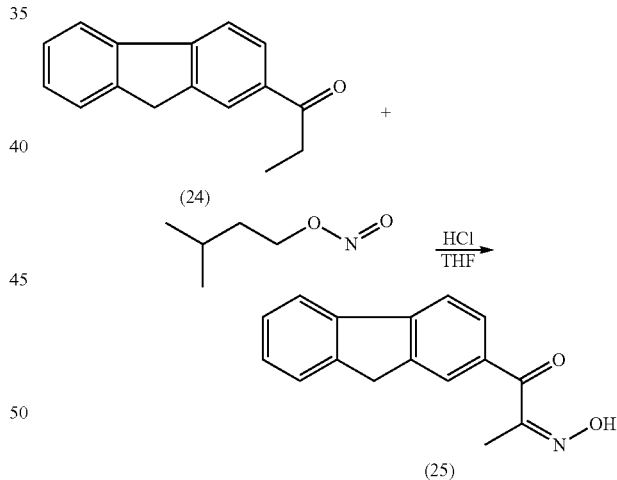

2.22 g (0.010 mol) 1-(9H-fluorene-2-yl)propan-1-one(24) was dissolved in 30 ml tetrahydrofuran (THF), 4.5 ml 4N HCl and 1.75 g (0.015 mol) isopentyl nitrite dissolved in 1,4-dioxane were added in a sequential order, and the reactants were stirred at 25° C. for 24 hours. Subsequently, 20 ml ethylacetate and 50 ml distilled water added to the reaction solution to extract an organic layer, then the extracted organic layer was dried with anhydrous magnesium sulfate and the solvent was distilled off under reduced pressure, and a resulting solid product was re-crystallized using 30 ml a mixed solvent of ethanol:ethylacetate (5:1) and dried to give 1.8 g (71.7%) 1-(9H-fluorene-2-yl)-1,2-propanedione-2-oxime(25) in pale grey.

1H NMR (δ ppm; CDCl3): 2.21 (3H, s), 3.95 (2H, s), 7.36-7.43 (2H, m), 7.57 (1H, d), 7.81-7.85 (2H, m), 7.98 (1H, d), 8.11 (1H, s), 8.15 (1H, s)

MS (m/e): 251

Reaction 3. Synthesis of 1-(9H-fluorene-2-yl)-1,2-propanedione-2-oxime-O-acetate(26)

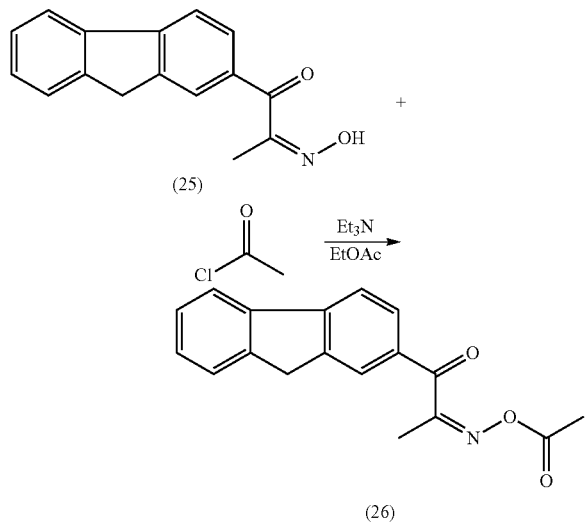

1.5 g (0.006 mol) 1-(9H-fluorene-2-yl)-1,2-propanedione-2-oxime(25) was dissolved in 25 ml ethylacetate under nitrogen atmosphere, and after the reactants were maintained at −5° C., 0.71 g (0.007 mmol) triethylamine was added, the reaction solution was stirred for 30 minutes, and a solution of 0.55 g (0.007 mol) acetyl chloride dissolved in 5 ml ethylacetate was added slowly over 30 minutes with care to avoid increasing the temperature of the reactants and stirred for 30 minutes. Subsequently, after 100 ml distilled water was added to the reactants slowly and stirred for about 30 minutes, an organic layer was separated, then the recovered organic layer was dried with anhydrous magnesium sulfate and the solvent was distilled off under reduced pressure to give 1.2 g (68.3%) 1-(9H-fluorene-2-yl)-1,2-propanedione-2-oxime-O-acetate(26) in pale yellow as a liquid having high viscosity.

1H NMR (δ ppm; CDCl3): 2.21 (3H, s), 2.32 (3H, s), 3.95 (2H, s) 7.36-7.43 (2H, m), 7.57 (1H, d), 7.81-7.85 (2H, m), 7.98 (1H, d), 8.15 (1H, s)

MS (m/e): 293

[Example of Preparation] Preparation of Binder Resin a) Preparation of Binder Resin 1

After putting 200 ml PGMEA and 1.5 g AIBN into a 500 ml polymerization container, acrylic monomers were added at a mole ratio of 20:20:40:20 of methacrylic acid, glycidylmethacrylate, methylmethacrylate and dicyclopentanylacrylate, respectively, with 40 wt % solids, followed by polymerization while stirring under nitrogen atmosphere at 70° C. for 5 hours to prepare acrylic polymer, i.e., binder resin 1. The average molecular weight of the resulting copolymer was found as being 25,000, and the degree of dispersion was found as being 2.0.

b) Preparation of Binder Resin 2

After putting 200 ml PGMEA and 1.0 g AIBN into a 500 ml polymerization container, acrylic monomers were added at a mole ratio of 40:20:20:20 of methacrylic acid, styrene, methylmethacrylate and cyclohexyl methacrylate, respectively, with 40 wt % solids, followed by polymerization while stirring under nitrogen atmosphere at 70° C. for 5 hours to synthesize a copolymer. 0.3 g N,N-dimethylaniline and 20 mole glycidylmethacrylate was put into this reactor, and stirred at 100° C. for 10 hours to prepare an acrylic polymer having an acrylic unsaturated bond on the side chain, i.e., binder resin 2. The average molecular weight of the resulting copolymer was found as being 20,000, and the degree of dispersion was found as being 2.1.

c) Preparation of Binder Resin 3

After putting 200 ml PGMEA and 1.0 g AIBN into a 500 ml polymerization container, acrylic monomers were added at a mole ratio of 40:20:20:20 of glycidylmethacrylate, styrene, methylmethacrylate and cyclohexylmethacrylate, respectively, with 40 wt % solids, followed by polymerization while stirring under nitrogen atmosphere at 70° C. for 5 hours to synthesize a copolymer. 0.3 g N,N-dimethylaniline and 20 mole acrylic acid was put into this reactor and stirred at 100° C. for 10 hours to prepare an acrylic polymer having an acrylic unsaturated bond on the side chain, i.e., binder resin 3. The average molecular weight of the resulting copolymer was found as being 18,000, and the degree of dispersion was found as being 1.8.

[Examples 15 to 24] Preparation of a Photoresist Composition

Binder resins 1 to 3; a photosensitive compound; compounds 5, 8, 14, and 17 as a photopolymerization initiator, and 0.1 wt % FC-430 (3M leveling agent) were put into a reaction mixing tank with a UV shield and a stirrer in a sequential order according to the ingredients and their content listed in Table 1, and after stirring at room temperature, balance of PGMEA as a solvent was added such that the total wt % of the composition is 100 wt %, to prepare a photoresist composition.

[Example 25] Preparation of a Photoresist Composition for a Black Matrix 20 wt % binder resin 1, 10 wt % dipentaerythritol hexaacrylate, 0.5 wt % compound 5, 50 wt % carbon black dispersion in PGMEA having 25 wt % solids, and 0.1 wt % FC-430 (3M leveling agent) were put into a reaction mixing tank with a UV shield and a stirrer in a sequential order, and after stirring at room temperature, balance of PGMEA as a solvent was added such that the total wt % of the composition is 100 wt %, to prepare a photoresist composition for a black matrix.

[Example 26] Preparation of a Red Photoresist Composition

A red photoresist composition was prepared by the same method as example 23 except that 50 wt % of Pigment Red 177 (P.R. 177) dispersion having 25 wt % solids was used in place of carbon black.

TABLE 1

| Example | Binder resin (wt %) | Polymerizable compound (wt %) | Photopolymerization initiator (wt %) | Additive (wt %) |
|---|---|---|---|---|
| 15 | 1 (40) | dipentaerythritol hexaacrylate (20) | compound 5(0.5) | FC-430(0.1) |
| 16 | 1 (40) | pentaerythritoltriacrylate (20) | compound 8(0.5) | FC-430(0.1) |
| 17 | 1 (40) | trimethylolpropanetriacrylate (10) ethyleneglycoldiacrylate (10) | compound 14(0.5) | FC-430(0.1) |
| 18 | 1 (40) | dipentaerythritolpentaacrylate (20) | compound 17(0.5) | FC-430(0.1) |
| 19 | 2 (40) | bisphenol-A diglycidyletheracrylic acid adduct (20) | compound 5(0.5) | FC-430(0.1) |
| 20 | 2 (40) | trimethylolpropanetriglycidyletheracrylic acid adduct (20) | compound 8(0.5) | FC-430(0.1) |
| 21 | 3 (40) | pentaerythritoltriacrylate (20) | compound 14(0.5) | FC-430(0.1) |
| 22 | 3 (40) | pentaerythritoltrimethacrylate(20) | compound 17(0.5) | FC-430(0.1) |
| 23 | 1 (20) 2 (20) | dipentaerythritol hexaacrylate (20) | compound 5(0.5) | FC-430(0.1) |
| 24 | 1 (20) 3 (20) | dipentaerythritol hexaacrylate (20) | compound 8(0.5) | FC-430(0.1) |
| 25 | 1 (20) | dipentaerythritol hexaacrylate (10) | compound 5(0.5) | FC-430 (0.1) carbon black (50) |
| 26 | 1 (20) | dipentaerythritol hexaacrylate (10) | compound 5(0.5) | FC-430 (0.1) P.R.177 (50) |

[Comparative Example 1] Preparation of a Photoresist Composition

A photoresist composition was prepared by the same method as example 15 except that photopolymerization initiator of Formula 3 was used in place of compound 5 as a photopolymerization initiator.

[Formula 3]

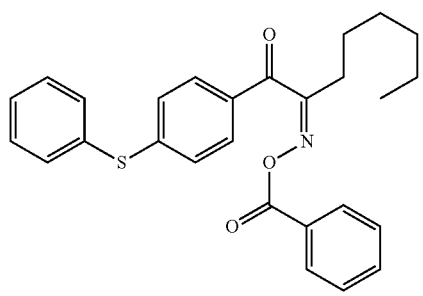

[Comparative Example 2] Preparation of a Photoresist Composition

A photoresist composition was prepared by the same method as example 15 except that "3-(acetoxyimino)-1-(6-nitro-9H-fluoren-3-yl)propane-1-one" was used in place of compound 5 as a photopolymerization initiator.

[Experimental Example] Photoresist Composition Evaluation

Evaluation of the photoresist compositions prepared in Examples 15 to 26 and Comparative Examples 1 and 2 was conducted on a glass substrate, the performance of the photoresist composition such as sensitivity, a residual film thickness, pattern stability, chemical resistance and elasticity was measured, and the evaluation results are shown in Table 2.

1) Sensitivity

The photoresist was spin-coated onto the glass substrate and dried at 100° C. on a hotplate for 1 minute, followed by exposure using a step mask and development in 0.04% KOH aqueous solution. The sensitivity was evaluated based on an exposure dose at which the thickness of a step mask pattern was maintained at 80% of an initial thickness.

2) Residual Film Thickness

After the photoresist composition was coated on the substrate using a spin coater, pre-baking was performed at 100° C. for 1 minute, followed by exposure at 365 nm, then post-baking was performed at 230° C. for 20 minutes, and a thickness ratio (%) of a resist film before and after post-baking was measured.

3) Pattern Stability

A silicon wafer with the photoresist pattern was cut in the direction perpendicular to a hole pattern, and a result of observing in the cross-sectional direction of the pattern using an electron microscope was shown. The side wall of the pattern was erected at an angle of 55 degrees or more with respect to the substrate, and no film reduction was determined as 'good' and an observed reduction of the film was determined as 'film reduction'.

4) Chemical Resistance

After the photoresist composition was coated on the substrate using a spin coater, a resist film formed through a pre-baking process and a post-baking process was dipped in a stripper solution at 40° C. for 10 minutes, and changes in transmittance and thickness of the resist film were observed. 2% or less of changes in transmittance and thickness was determined as 'good', and more than 2% of changes in transmittance and thickness was determined as 'bad'.

5) Ductility

The photoresist composition was coated on the substrate using a spin coater, followed by pre-baking at 100° C. for 1 minute, exposure at the sensitivity of the photoresist, and development in a KOH aqueous solution, to form a pattern of 20 um×20 um. The formed pattern was crosslinked by post-baking at 230° C. for 20 minutes, and the pattern was measured using a nano indentor to determine elasticity. Measurements of the nano indentor were made at 5 g.f loads, and 500 nm or more of total variation was determined as 'good', and less than 500 nm of total variation was determined as 'bad'.

TABLE 2

| Example | Sensitivity (mJ/cm²) | Residual film thickness (%) | Pattern stability | Chemical resistance | Ductility |
|---|---|---|---|---|---|
| 15 | 40 | 91 | good | good | good |
| 16 | 50 | 92 | good | good | good |
| 17 | 45 | 91 | good | good | good |
| 18 | 55 | 90 | good | good | good |
| 19 | 35 | 93 | good | good | good |
| 20 | 40 | 91 | good | good | good |
| 21 | 40 | 91 | good | good | good |
| 22 | 50 | 92 | good | good | good |
| 23 | 30 | 93 | good | good | good |
| 24 | 35 | 93 | good | good | good |

TABLE 2-continued

| Example | Sensitivity (mJ/cm$^2$) | Residual film thickness (%) | Pattern stability | Chemical resistance | Ductility |
|---|---|---|---|---|---|
| 25 | 60 | 90 | good | good | good |
| 26 | 60 | 91 | good | good | good |
| Comparative example 1 | 200 | 87 | film reduction | bad | good |
| Comparative example 2 | 250 | 80 | film reduction | bad | bad |

What is claimed is:

1. A fluorenyl β-oxime ester derivative compound of Formula 1:

[Formula 1]

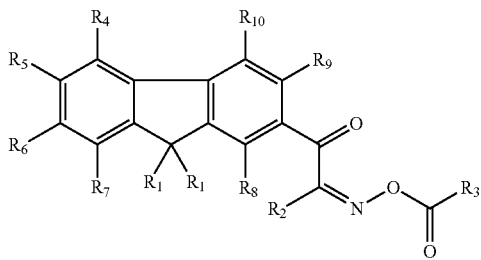

wherein $R_1$ to $R_{10}$ are each independently hydrogen, halogen, an alkyl group having 1-20 carbon atoms, an aryl group having 6-20 carbon atoms, an alkoxy group having 1-20 carbon atoms, an arylalkyl group having 7-40 carbon atoms, a hydroxyalkyl group having 1-20 carbon atoms, a hydroxyalkoxyalkyl group having 2-40 carbon atoms or a cycloalkyl group having 3-20 carbon atoms.

2. The fluorenyl β-oxime ester derivative compound according to claim 1, wherein the $R_1$ to $R_{10}$ are each independently hydrogen, bromo, chloro, iodo, a methyl group, an ethyl group, an n-propyl group, an i-propyl group, an n-butyl group, an i-butyl group, a t-butyl group, an n-pentyl group, an i-pentyl group, an n-hexyl group, an, i-hexyl group, a phenyl group, a naphthyl group, a biphenyl group, a terphenyl group, an antryl group, an indenyl group, a phenanthryl group, a methoxy group, an ethoxy group, an n-propyloxy group, an i-propyloxy group, an n-butoxy group, an i-butoxy group, a t-butoxy group, a hydroxymethyl group, a hydroxyethyl group, a hydroxyn-propyl group, a hydroxyn-butyl group, a hydroxyl i-butyl group, a hydroxyl n-pentyl group, a hydroxyl i-pentyl group, a hydroxyl n-hexyl group, a hydroxyl i-hexyl group, a hydroxymethoxymethyl group, a hydroxymethoxyethyl group, a hydroxymethoxypropyl group, a hydroxymethoxybutyl group, a hydroxyethoxymethyl group, a hydroxyethoxyethyl group, a hydroxyethoxypropyl group, a hydroxyethoxybutyl group, a hydroxyethoxypentyl group or a hydroxyethoxyhexyl group.

3. The fluorenyl β-oxime ester derivative compound according to claim 1, wherein the $R_1$ is hydrogen, a methyl group, an ethyl group, a propyl group, or a butyl group; the $R_2$ is a methyl group, an ethyl group, or a propyl group; the $R_3$ is a methyl group, an ethyl group, a propyl group, or a butyl group; and the $R_4$ to $R_{10}$ are hydrogen.

4. A photopolymerization initiator comprising the fluorenyl β-oxime ester derivative compound of claim 1 as an active ingredient.

5. A photoresist composition comprising the fluorenyl β-oxime ester derivative compound of claim 1, an acrylic polymer or an acrylic polymer having an acrylic unsaturated bond on a side chain, a polymerizable compound having an ethylenically unsaturated bond, and a solvent.

6. The photoresist composition according to claim 5, wherein the photoresist composition comprises 0.01 to 10 wt % of a fluorenyl β-oxime ester derivative compound, 3 to 50 wt % of an acrylic polymer or an acrylic polymer having an acrylic unsaturated bond on a side chain, 0.001 to 40 wt % of a polymerizable compound having an ethylenically unsaturated bond, and 10 to 95 wt % of a solvent.

7. The photoresist composition according to claim 5, wherein the photoresist composition further comprises carbon black.

8. The photoresist composition according to claim 5, wherein the photoresist composition further comprises a colorant.

9. A molded product formed by coating the photoresist composition of claim 5.

10. The molded product according to claim 9, wherein the molded product is a black matrix or a color filter.

* * * * *